United States Patent
Chilcote et al.

(10) Patent No.: US 7,553,639 B2
(45) Date of Patent: Jun. 30, 2009

(54) ALPHA-SYNUCLEIN KINASE

(75) Inventors: Tami J. Chilcote, San Francisco, CA (US); Kelly Banducci, Pleasanton, CA (US); Normand L. Frigon, Jr., South San Francisco, CA (US); Guriqbal S. Basi, Palo Alto, CA (US); John P. Anderson, San Francisco, CA (US); Jason Goldstein, Decatur, GA (US); Irene Griswold-Prenner, San Francisco, CA (US); David Chereau, San Mateo, CA (US)

(73) Assignee: Elan Pharma International Limited, Monksland, Athlone, County Westmeath (IE)

( * ) Notice: Subject to any disclaimer, the term of this patent is extended or adjusted under 35 U.S.C. 154(b) by 56 days.

(21) Appl. No.: 11/669,093

(22) Filed: Jan. 30, 2007

(65) Prior Publication Data

US 2008/0160011 A1 Jul. 3, 2008

Related U.S. Application Data

(60) Provisional application No. 60/764,000, filed on Jan. 31, 2006.

(51) Int. Cl.
*C12P 21/06* (2006.01)
*C07K 14/00* (2006.01)

(52) U.S. Cl. ............ 435/69.1; 435/320.1; 435/252.3; 536/23.1; 530/350

(58) Field of Classification Search ................ None
See application file for complete search history.

(56) References Cited

U.S. PATENT DOCUMENTS

| | | | |
|---|---|---|---|
| 6,861,422 | B2 | 3/2005 | Hoffmann et al. |
| 2004/0176380 | A1 | 9/2004 | Hoffmann et al. |
| 2005/0014761 | A1 | 1/2005 | Hoffmann et al. |
| 2006/0025411 | A1 | 2/2006 | Hoffmann et al. |
| 2006/0057652 | A1 | 3/2006 | Green et al. |
| 2006/0079503 | A1 | 4/2006 | Schwede et al. |
| 2006/0223833 | A1 | 10/2006 | Schulze et al. |
| 2007/0010565 | A1 | 1/2007 | Prien et al. |
| 2007/0010566 | A1 | 1/2007 | Prien et al. |
| 2007/0037862 | A1 | 2/2007 | Siemeister et al. |
| 2007/0135387 | A1 | 6/2007 | Michaelides et al. |
| 2007/0179177 | A1 | 8/2007 | Brenchley et al. |
| 2007/0203143 | A1 | 8/2007 | Sheppard et al. |
| 2008/0160011 | A1 | 7/2008 | Chilcote et al. |
| 2008/0300206 | A1 | 12/2008 | Anderson et al. |

FOREIGN PATENT DOCUMENTS

| | | |
|---|---|---|
| WO | WO 01/60794 A2 | 8/2001 |
| WO | WO 2004/069175 A2 | 8/2004 |
| WO | WO 2006/073734 A2 | 7/2006 |
| WO | WO 2006/124892 A2 | 11/2006 |
| WO | WO 2007/089862 A2 | 8/2007 |

OTHER PUBLICATIONS

Inglis et al. Polo-like kinase 2 (PLK2) phosphorylates alpha-synuclein at serine 129 in the central nervous system. J. Biol. Chem. Papers in Press, Published Nov. 12, 2008.*
Inglis et al., "Polo-like kinase 2 (PLK2) phosphorylates alpha-synuclein at serine 129 in the central nervous system," J.Biol. Chem. Papers in Press, pp. 1-11 (2008).
Johnson et al., "Pharmacological and Functional Comparison of the Polo-like Kinase Family: Insight into Inhibitor and Substrate Specificity, Biochemistry," 46:9551-9563 (2007).
Naoto et al., "Serine 129 phosohorylation of alpha-synuclein induces unfolded protein response-mediated cell death," *Journal of Biological Chemistry*, 283(34):23179-23188 (2008), Biosis Previews, Abstract only.
PCT International Preliminary Report on Patentability (Chapter I) of Oct. 28, 2008 with Written Opinion for application PCT/US2007/002685.
PCT Search Report of Sep. 26, 2008 for application PCT/US2007/002685.
Steegmaier et al., "BI 2536, a Potent and Selective Inhibitor of Polo-like Kinase 1, Inhibits Tumor Growth in Vivo," Current Biology, 17:316-322 (2007).
Winkles et al., "Differential regulation of polo-like kinase 1, 2, 3, and 4 gene expression in mammalian cells and tissues," Oncogene, 24:260-266 (2005).

* cited by examiner

*Primary Examiner*—Karen Cochrane Carlson
(74) *Attorney, Agent, or Firm*—Townsend and Townsend and Crew LLP

(57) ABSTRACT

The invention provides agents and methods for treatment of diseases associated with Lewy body diseases (LBDs) in the brain of a patient. Preferred agents include inhibitors of PLK2 and GRK6 kinases.

7 Claims, 12 Drawing Sheets total AS pSer 129 AS.

GRK Analysis Normalized to Molar Ratio (1:200 kinase: AS)

total AS

GRK Analysis Normalized to Molar Ratio (1:200 kinase: AS)

Phospho S129 AS

Normalized to Activity Units (nmol phosphate into µM synthetic peptide)

total AS

Normalized to Activity Units (nmol phosphate into µM synthetic peptide)

pSer129 AS

GRK Analysis Normalized to Molar Ratio (1:200 kinase: AS)

total AS

GRK Analysis Normalized to Molar Ratio (1:200 kinase: AS)

Phospho S129 AS

Total AS   A

Phospho S129 AS   B

Total AS   A

Phospho S87 AS   B

ALPHA-SYNUCLEIN KINASE

RELATED APPLICATIONS

This application claims priority to U.S. Provisional application 60/764,000, filed Jan. 31, 2006, herein incorporated by reference in its entirety for all purposes.

BACKGROUND OF THE INVENTION

Lewy body diseases (LBDs) are characterized by degeneration of the dopaminergic system, motor alterations, cognitive impairment, and formation of Lewy bodies (LBs). (McKeith et al., *Clinical and pathological diagnosis of dementia with Lewy bodies (DLB): Report of the CDLB International Workshop, Neurology* (1996) 47:1113-24). LBDs include Parkinson's disease, Diffuse Lewy body disease (DLBD), Lewy body variant of Alzheimer's disease (LBV), and combined Parkinson's disease (PD) and Alzheimer's disease (AD) and the syndromes identified as multiple system atrophy (MSA). Dementia with Lewy bodies (DLB) is a term coined to reconcile differences in the terminology of LBDs. Disorders with LBs continue to be a common cause for movement disorders and cognitive deterioration in the aging population (Galasko et al., *Clinical-neuropathological correlations in Alzheimer's disease and related dementias. Arch. Neurol.* (1994) 51:888-95). Although their incidence continues to increase creating a serious public health problem, to date these disorders lack approved treatments (Tanner et al., *Epidemiology of Parkinson's disease and akinetic syndromes, Curr. Opin. Neurol.* (2000) 13:427-30). The cause for LBD's is controversial and multiple factors have been proposed to play a role, including various neurotoxins and genetic susceptibility factors.

In recent years, new hope for understanding the pathogenesis of LBD has emerged. Specifically, several studies have shown that the synaptic protein alpha-synuclein plays a central role in PD pathogenesis since: (1) this protein accumulates in LBs (Spillantini et al., *Nature* (1997) 388:839-40; Takeda et al., *J. Pathol.* (1998) 152:367-72; Wakabayashi et al., *Neurosci. Lett.* (1997) 239:45-8), (2) mutations in the alpha-synuclein gene co-segregate with rare familial forms of parkinsonism (Kruger et al., *Nature Gen.* (1998) 18:106-8; Polymeropoulos, et al., *Science* (1997) 276:2045-7) and, (3) its overexpression in transgenic mice (Masliah et al., *Science* (2000) 287:1265-9) and *Drosophila* (Feany et al., *Nature* (2000) 404:394-8) mimics several pathological aspects of PD. Thus, the fact that accumulation of alpha-synuclein in the brain is associated with similar morphological and neurological alterations in species as diverse as humans, mice, and flies suggests that this molecule contributes to the development of PD.

BRIEF SUMMARY OF THE INVENTION

In one aspect, the invention provides methods of screening an agent for activity for treating a Lewy Body disease (LBD). Such diseases include Parkinson's disease (PD), Diffuse Lewy body disease (DLBD), Lewy body variant of Alzheimer's disease (LBV), and combined PD and Alzheimer's disease (AD) and the syndromes identified as multiple system atrophy (MSA). Some methods entail identifying an agent that modulates the activity or expression of a kinase shown in Table 1A, B; C, Table 2, Table 12 or Table 13, and determining whether the agent shows activity useful in treating LBD in an animal model of the disease. In some methods the modulation is inhibition. In some methods, step (a) involves identifying whether the agent inhibits the kinase. In some methods, step (a) is performed in a cell transformed with a nucleic acid expressing the kinase and/or alpha-synuclein. In some methods, step (a) is performed in vitro. In some methods, step (b) is performed in a transgenic animal model of LBD disease, and the transgenic animal may have a transgene expressing human alpha-synuclein. Preferably, the kinase is at least one of: APEG1, PLK2, CDC7L1, PRKG1, MAPK13, GAK, RHOK, ADRBK1, ADRBK2, GRK2L, GRK5, GRK6, GRK7, IKBKB, CKII and MET and the modulation is inhibition. More preferably, the kinase is PLK2 or GRK6 and the modulation is inhibition. More preferably, the kinase is PLK2. Preferably in some methods, the kinase is PRKG1, MAPK13, or GAK and the modulation is activation. In some aspects, step (b) involves contacting the transgenic animal with the agent and determining whether the agent inhibits formation of deposits of alpha-synuclein relative to a control transgenic animal not treated with the agent.

In another aspect, the invention provides methods of effecting treatment or prophylaxis of an LBD. Some examples of the method involve administering to a patient suffering from or at risk of the disease, an effective regime of an agent effective to modulate activity or expression of a kinase. The kinase can be one of those shown in Table 1A, B or C, Table 2, Table 12 or Table 13. Preferably, the agent is an antibody to the kinase, a zinc finger protein that modulates expression of the kinase, or an antisense RNA, siRNA, ribozyme or RNA having a sequence complementary to a nucleic acid sequence of the kinase. In some methods, the modulation is inhibition, and preferably, the kinase is at least one of the following: APEG1, PLK2, CDC7L1, RHOK, ADRBK1, ADRBK2, GRK2L, GRK5, GRK6, GRK7, IKBKB, CKII and MET. More preferably, the kinase is PLK2 or GRK6. More preferably, the kinase is PLK2. In some of the methods, the kinase is at least one of: PRKG1, MAPK13, and GAK, and the modulation is activation.

In another aspect, the invention provides methods of identifying a kinase that phosphorylates alpha-synuclein by transfecting a cell expressing alpha-synuclein with a nucleic acid having a sequence complementary to a gene encoding a kinase or zinc finger protein that specifically binds to the gene. The transfected nucleic acid or zinc finger protein inhibits expression of the kinase; and an amount of phosphorylated alpha-synuclein the cell can then be measured relative to a control cell not transfected with the siRNA or nucleic acid encoding the same. In this case, a reduction in phosphorylated alpha-synuclein will provide an indication that the kinase phosphorylates alpha-synuclein. Some methods also include measuring an amount of alpha-synuclein produced by the cell relative to a control cell not transfected with the nucleic acid. In some methods, the nucleic acid is an siRNA or a DNA molecule encoding the same.

In other aspects, the invention provides methods of method of screening an agent for activity for treating a Lewy Body disease (LBD), by identifying an agent that modulates the activity or expression of synphilin, and determining whether the agent shows activity useful in treating LBD in an animal model of the disease.

In other aspects, the invention provides methods for producing Ser-129 phosphorylated-alpha synuclein, by providing a plasmid encoding alpha-synuclein and a plasmid encoding PLK2 in a bacterial cell, culturing the cell so that the plasmids are co-expressing to produce alpha synuclein and PLK2 so that the PLK2 phosphorylates the alpha-synuclein in a bacterial cell, and isolating phosphorylated alpha synuclein from the cell.

BRIEF DESCRIPTION OF THE DRAWINGS

FIG. 1A shows total alpha-synuclein, FIG. 1B shows phosphorylation of the pser-129 of alpha-synuclein and FIG. 1C shows phosphorylation of the pser-87 of alpha-synuclein.

FIG. 1D shows total alpha-synuclein, FIG. 1E shows phosphorylation of the pser-129 (phospho-ser-129) of alpha-synuclein and FIG. 1F shows phosphorylation of the pser-87 (phospho-ser-87) of alpha-synuclein.

FIG. 2A shows the total AS.

FIG. 2A shows the total AS. FIG. 3B shows Serine 129. FIG. 3C shows Serine 87.

FIG. 4A shows the total AS.

DEFINITIONS

Figure 1A:
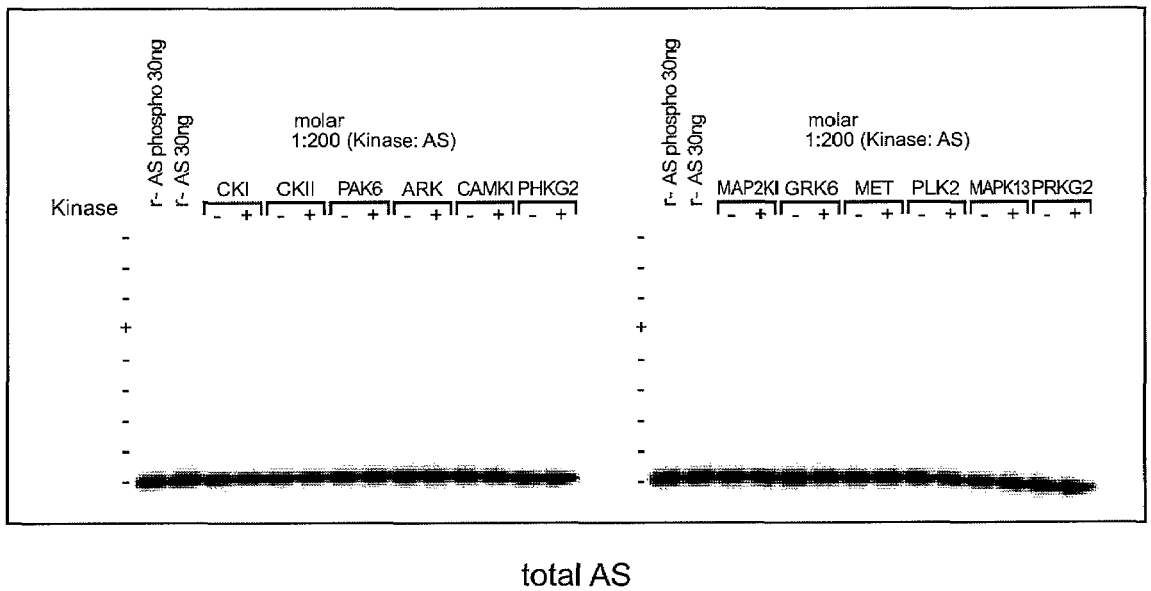
FIGS. 1A-C show the results of the in vitro phosphorylation assay for alpha-synuclein phosphorylation by a variety of recombinant kinases.

The term "agent" is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity.

A "pharmacological" activity means that an agent exhibits an activity in a screening system that indicates that the agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

A Lewy-like body is a water/detergent-insoluble deposit of alpha-synuclein found in a transgenic animal that resembles some or all of the characteristics of a Lewy body found in human patients. The preferred characteristics are a compact alpha-synuclein positive inclusion. These inclusions preferably form in an age-dependent manner. The formation of alpha-synuclein positive inclusions preferably results in observable cellular pathology, leading to loss of functionality of affected neurons. Loss of function of affected neurons can be determined through behavioral tests, neuropharmacological response evaluation and electrophysiology.

The phrase "specifically binds" refers to a binding reaction which is determinative of the presence of the protein in the presence of a heterogeneous population of proteins and other biologics. Thus, under designated conditions, a specified ligand binds preferentially to a particular protein and does not bind in a significant amount to other proteins present in the sample. A molecule such as an antibody that specifically binds to a protein often has an association constant of at least $10^6 M^{-1}$ or $10^7 M^{-1}$, preferably $10^8 M^{-1}$ to $10^9 M^{-1}$, and more preferably, about $10^{10} M^{-1}$ to $10^{11} M^{-1}$ or higher. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

For sequence comparison, typically one sequence acts as a reference sequence, to which test sequences are compared. When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., *supra*).

Another example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., *supra.*). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

For purposes of classifying amino acids substitutions as conservative or non-conservative, amino acids are grouped as follows: Group I (hydrophobic side chains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained.

The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

A symptom of a disorder means a phenomenon experienced by an individual having the disorder indicating a departure from normal function, sensation or appearance.

A sign of a disorder is any bodily manifestation that serves to indicate presence or risk of a disorder.

The term "patient" includes human and other mammalian subjects that receive either prophylactic or therapeutic treatment.

Compositions or methods "comprising" one or more recited elements may include other elements not specifically recited. For example, a composition that comprises alpha-synuclein peptide encompasses both an isolated alpha-synuclein peptide and alpha-synuclein peptide as a component of a larger polypeptide sequence.

Unless otherwise apparent from the context, each embodiment, element, step or feature of the invention can be used in combination with any other.

DETAILED DESCRIPTION OF THE INVENTION

I. General

The invention is premised in part on the insight that Lewy Body diseases (LBDs) can be inhibited by inhibiting one or more kinases that phosphorylate alpha-synuclein and/or inhibit its production. Alpha-synuclein is the principal protein present in Lewy bodies (LBs). Although practice of the invention is not dependent on an understanding of mechanism, it is believed that phosphorylation of alpha-synuclein at codon 129 is one of a series of molecular events leading to formation of intracellular deposits of alpha-synuclein. Alpha-synuclein phosphorylated at ser-129 is highly enriched in Lewy bodies (LBs) in Diffuse Lewy body disease (DLBD), multiple system atrophy (MSA) and a familial form of Parkinson's Disease (PD). The abnormal accumulation of phospho-alpha-synuclein in LBs indicates that phospho-synuclein is a pathogenic species that drives LB formation, and that the kinase(s) responsible for its phosphorylation or which regulate production of alpha-synuclein itself are therapeutic target(s) for treatment of multiple synucleinopathies. Other events in this series likely include proteolytic cleavages following phosphorylation (see WO 2005/013889, filed May 19, 2004). The present application reports identification of several kinases whose inhibition is accompanied by a reduction of phosphorylation in alpha-synuclein and/or a reduction in total alpha-synuclein level. The invention provides methods of identifying modulators of the activity and expression of these kinases, and methods of treating Lewy body diseases.

II. Kinases of the Invention

Tables 1A, 1B and 1C show proteins whose inhibition modulates the phosphorylation at position ser-129. Table 1A shows kinases that can phosphorylate serine and/or threonine residues and sometimes tyrosine. Table 1B shows tyrosine kinases that cannot (so far as is known) modify serine residues. Table 1C shows proteins not known to have kinase activity. Kinases from the upper portion of Table 1A are candidates for direct phosphorylation of ser-129 of alpha-synuclein. Kinases from the upper part of Table 1B are also useful therapeutic targets via roles indirectly phosphorylating alpha-synuclein. Proteins in the upper part of Table 1C are also useful therapeutic targets for the same reason. Cols. 1, 2 and 3 of each table indicate the gene name, kinase name and Genbank accession number of kinases. The next column indicates whether inhibition of the kinase decreased ("down") or increased ("up") phosphorylation. The next three columns indicate the number of standard deviations the measured level of phosphorylation departs from the mean in three independent experiments. The final two columns indicate the kinase family (i.e., amino acid specificity) and group.

Tables 2 and 3 show kinases whose inhibition modulates the overall levels of human alpha-synuclein without changing the percentage of phosphorylation. Table 2 shows all of the kinases with the strongest reduction in levels of human alpha-synuclein. The columns are labeled similarly to Tables 1A, 1B and 1C.

Tables 4 and 5 show kinases from Tables 1, 2 and 3 that were confirmed in the Examples to modulate overall levels of human alpha-synuclein. The kinases that were verified include PLK2, APEG1, CDC7L1, MET, GRK1, 2, 6, and 7 as kinases that phosphorylate alpha-synuclein directly or indirectly. The kinases that were found to increase alpha-synuclein phosphorylation when inhibited, PRKG1, MAPK13, and GAK, are likely to function as negative regulators of alpha-synuclein phosphorylation. Further data from phosphorylation studies in vitro identified PKL2, GRK2, 5, 6, and 7 as capable of phosphorylating alpha-synuclein in vitro and also identified CKII and IKBKB. Further studies in tissue culture showed that PLK2 and GPRK6 could directly phosphorylate alpha-synuclein in tissue culture. These data were substantiated with immunohistochemistry. In summary, PLK2 and, to a lesser extent, GRK6 are particularly preferred targets for therapeutic intervention in Lewy body diseases because they can directly phosphorylate alpha-synuclein. Agents that inhibit PLK2 and GRK6 also inhibit phosphorylation of alpha-synuclein and thus can be used in treatment or prophylaxis of Lewy body disease. APEG1, CDC7L1, MET, IKBKB, CKII, GRK1, GRK2, GRK6 and GRK7 are also targets for therapeutic intervention in Lewy body diseases because they are likely to be indirect activators of the direct kinase(s). Thus, agents that inhibit APEG1, CDC7L1, MET, IKBKB, CKII, GRK1, GRK2, GRK6 and GRK7 also inhibit phosphorylation of alpha-synuclein and can be used for treatment or prophylaxis of Lewy body disease. PRKG1, MAPK13, and GAK are negative regulators of the phosphorylation of alpha-synuclein. Thus, agents that activate these kinases decrease phosphorylation of alpha-synuclein and can be used in treatment or prophylaxis of Lewy body disease.

PLK2, also called SNK, is a Polo like kinase that is a G1 cell cycle protein, has a rapid turnover in cells, and is expressed in brain where it is involved in synaptic plasticity. For purposes of consistency, the name PLK2 is used throughout the present patent application. When PLK2 is activated, it is targeted to dendrites of activated neurons, where it is believed to phosphorylate proteins in the synaptic terminals. An exemplary accession number for PLK2 is provided Table 1A. The sequence for PLK2 can also be found in any one of Ma, et al. Mol. Cell. Biol. 23 (19), 6936-6943 (2003), Burns, et al. Mol. Cell. Biol. 23 (16), 5556-5571 (2003), Matsuda, et al. Oncogene 22 (21), 3307-3318 (2003), Shimizu-Yoshida et al. Biochem. Biophys. Res. Commun. 289 (2), 491-498 (2001), Liby, et al. DNA seq. 11 (6), 527-533 (2001), Holtrich, et al. Oncogene 19 (42), 4832-4839, Ouyang, et al. Oncogene 18 (44), 6029-6036 (1999), and Kauselmann, et al. EMBO J. 18 (20), 5528-5539; reference to an amino acid or nucleic acid sequence of PLK2 includes the sequences of any of these references or allelic variants thereof.

GRK6, also called GPRK6, is a G protein-coupled receptor kinase and is involved in signal transduction. G protein-coupled receptor kinases phosphorylate and desensitize ligand-activated G protein-coupled receptors. GRK6 expression has previously been shown to be significantly elevated in the MPTP-lesioned group in most brain regions. For the purposes of consistency, the name GRK6 will be used throughout the present patent application. An exemplary accession number is provided in Table 1A. The sequence for GRK6 can be found in any one of Teli, et al., Anesthesiology 98 (2), 343-348 (2003); Miyagawa, et al., Biophys. Res. Commun. 300 (3), 669-673 (2003); Gaudreau, et al., J. Biol. Chem. 277 (35), 31567-31576 (2002); Grange-Midroit, et al., Brain Res. Mol. Brain. Res. 101 (1-2), 39-51 (2002); Willets, et al., J. Biol. Chem. 277 (18), 15523-15529 (2002); Blaukat, et al., J. Biol. Chem. 276 (44), 40431-40440 (2001); Zhou, et al., J. Pharmacol. Exp. Ther. 298 (3), 1243-1251 (2001); Pronin, et al., J. Biol. Chem. 275 (34), 26515-26522 (2000); Tiruppathi, Proc. Natl. Acad. Sci. U.S.A., 97 (13), 7440-7445 (2000); Premont, et al. J. Biol. Chem., 274 (41), 29381-29389 (1999); Brenninkmeijer, et al., J. Endocrinol. 162 (3), 401-408 (1999); Hall, et al., J. Biol. Chem. 274 (34), 24328-24334 (1999); Lazari, et al., Mol. Endocrinol. 13 (6), 866-878 (1999); Milcent, et al., Biochem. Biophys. Res. Commun. 259 (1), 224-229 (1999); Premont, Proc. Natl. Acad. Sci. U.S.A. 95 (24), 14082-14087 (1998); Stoffel, et al., Biochemistry 37 (46), 16053-16059 (1998); Loudon, et al., J. Biol. Chem. 272 (43), 27422-27427 (1997); Freedman, et al., J. Biol. Chem. 272 (28), 17734-17743 (1997); Bullrich, et al., Cytogenet. Cell Genet. 70 (3-4), 250-254 (1995); Stoffel, et al.; J. Biol. Chem. 269 (45), 27791-27794 (1994); Loudon, et al., J. Biol. Chem. 269 (36), 22691-22697 (1994); Haribabu and Snyderman, Proc. Natl. Acad. Sci. U.S.A. 90 (20), 9398-9402 (1993); and Benovic and Gomez, J. Biol. Chem. 268 (26), 19521-19527 (1993); reference to the amino acid or nucleic acid sequence of GRK6 includes the amino acid or nucleic acid sequence of any of these references and allelic variants thereof.

Casein kinase II (also called CKII, CSNK2 and CSNKII) has been reported to phosphorylate alpha-synuclein. For consistency, the name CKII will be used herein. The sequence for CKII has been provided in genbank under the following accession numbers: NM_001896, NM_001320 and/or can be found in any one of: Panasyu, et al. J. Biol. Chem. 281 (42), 31188-31201 (2006); Salvi, et al. FEBS Lett. 580 (16), 3948-3952 (2006); Lim et al. Cell 125 (4), 801-814 (2006); Llorens, et al. Biochem. J. 394 (Pt. 1), 227-236, (2006); Bjorling-Poulsen, et al. Oncogene 24 (40), 6194-6200 (2005); Schubert, et al. Eur. J. Biochem. 204 (2), 875-883 (1991); Voss, et al. J. Biol. Chem. 266 (21), 13706-13711 (1991); Yang-Feng, et al. Genomics 8 (4), 741-742 (1990); Heller-Harrison, et al. Biochemistry 28 (23), 9053-9058 (1989); Ackermann, et al. Mol. Cell. Biochem. 274 (1-2), 91-101 (2005); Barrios-Rodiles, et al. Science 307 (5715), 1621-1625 (2005); Andersen, et al. Nature 433 (7021), 77-83 (2005); Ballif, et al. Mol. Cell. Proteomics, 3 (11), 1093-1101 (2004); Beausoleil, et al. PNAS, USA 101 (33), 12130-12135 (2004); Marais, et al. EMBO J. 11 (1), 97-105 (1992). Reference to the amino acid or nucleic acid sequence of CKII includes the amino acid or nucleic acid sequence of any of these references and allelic variants thereof IKBKB and the related IKBKA are positive regulators of the NFkB inflammatory pathway. The sequence for IKBKB has been provided in genbank under the following accession number: NM_001556 and/or can be found in any one of: Caterino, et al. FEBS Lett. 580 (28-29), 6527-6532 (2006); Castle, et al. Genome Biol. 4 (10), R66 (2003); Satoh, et al. Biochim, Biophys. Acta 1600 (103), 61-67 (2002), Caohuy, and Pollard, J. Biol. Chem. 277 (28), 25217-25225 (2002); Yu, et al. J. Biol. Chem. 277 (18), 15819-15827 (2002); Selbert, et al. J. Cell. Sci. 108 (Pt.1), 85095 (1995); Shirvan, et al. Biochemistry 33 (22), 6888-6901 (1994); Creutz, et al. Biochem. Biophys. Res. Commun. 184 (1), 347-352 (1992); Megendzo, et al. J. Biol. Chem. 266 (5), 3228-3232 (1991); Burns, et al. PNAS, USA 86 (10), 3798-3802 (1989). Reference to the amino acid or nucleic acid sequence of IKBKB includes the amino acid or nucleic acid sequence of any of these references and allelic variants thereof.

Synphilin is a synuclein-associated protein that has been shown to bind alpha-synuclein. Although not a kinase itself, Synphilin was found herein to promote phosphorylation of synuclein particularly in combination with PLK2. The synphilin appeared to promote phosphorylation of synuclein in a PLK2-dependent manner. The sequence for synphilin has been provided in genbank under the following accession number: NM_005460 and/or can be found in any one of: Tanji, et al. Am. J. Pathol. 169 (2), 553-565 (2006); Eyal, et al. PNAS, USA 103 (15), 5917-5922 (2006); Avraham, et al. J. Biol. Chem. 280 (52), 42877-42886 (2005); Bandopadhyay, et al. Neurobiol. Dis. 20 (2), 401-411 (2005); Lim et al. J. Neurosci. 25 (8), 2002-2009 (2005); Ribeiro, et al. J. Biol. Chem. 277 (26), 23927-23933 (2002); Chung, et al. Nat. Med. 7 (10), 1144-1150 (2001); Engelender, et al. Mamm. Genome 11 (9), 763-766 (2000); Engelender, et al. Nat. Genet. 22 (1), 110-114 (1999). Reference to the amino acid or nucleic acid sequence of synphilin includes the amino acid or nucleic acid sequence of any of these references and allelic variants thereof III. Alpha-Synuclein Isolation Human alpha-synuclein is a polypeptide of 140 amino acids having the following amino acid sequence:

```
                                              (SEQ ID NO:1)
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
```

(Ueda et al., Proc. Natl. Acad. Sci. USA (1993) 90:11282-6).; GenBank accession number: P37840). The protein has three recognized domains, a KTKE repeat domain covering amino acids 1-61, a NAC (Non-amyloid component) domain running from about amino acids 60-95, and a C-terminal acidic domain running from about amino acid 98 to 140.

Unless otherwise apparent from the context, reference to alpha-synuclein includes the natural human amino acid sequence indicated above as well as analogs including allelic, species and induced variants (e.g., E83Q, A90V, A76T) having at least 90% sequence identity to natural human alpha-synuclein. Amino acids of analogs are assigned the same numbers as corresponding amino acids in the natural human sequence when the analog and human sequence are maximally aligned. Analogs typically differ from naturally occurring peptides at one, two or a few positions, often by virtue of conservative substitutions. Some natural allelic variants are genetically associated with hereditary LBD. The term "allelic variant" is used to refer to variations between genes of different individuals in the same species and corresponding variations in proteins encoded by the genes. Allelic variants include familial mutants or variants, such as E46K, A30P and A53T (the first letter indicates the amino acid in SEQ ID NO:1, the number is the codon position in SEQ ID NO:1, and the second letter is the amino acid in the allelic variant). Analogs can include any combination of allelic variants. The A53T variation is associated with enhanced levels of phosphorylation at position 129 of alpha-synuclein in an individual having the mutation relative to the norm of phosphorylation in undiseased individuals who lack the mutation.

Alpha-synuclein, its fragments, and analogs can be synthesized by solid phase peptide synthesis or recombinant expression, or can be obtained from natural sources. Automatic peptide synthesizers are commercially available from numerous suppliers, such as Applied Biosystems, Foster City, Calif. Recombinant expression can be in bacteria, such as $E.$ $coli$, yeast, insect cells or mammalian cells. Procedures for recombinant expression are described by Sambrook et al., *Molecular Cloning: A Laboratory Manual* (C.S.H.P. Press, NY 2d ed., 1989).

A method was developed herein to prepare large amounts of wild-type phospho-S129 alpha-synuclein, mutant and/or familial forms in a bacterial expression system. When recombinant hPLK2 was co-expressed with alpha-synuclein in bacteria, the phospho-S129 alpha-synuclein that was produced in the cell was recovered with a very high yield and purity. This is because, unlike most $E.$ $coli$ proteins, the alpha-synuclein could resist heating. After boiling of the bacterial lysate, alpha-synuclein purity reached about 95% before chromatography.

To co-express recombinant protein in a bacterial system, the plasmids harboring each gene of interest were chosen be compatible within the bacterial cell by ensuring that they possessed a different origin of replication and a different antibiotic selection. The alpha-synuclein gene was subcloned into a pDEST24 compatible vector, pCDF1b. BL21-DE3 bacteria were then co-transformed with both the pDEST24 containing wild-type hPLK2 or hPLK2 constitutive mutant constructs without a GST tag and the pCDF1b/AS plasmid. The bacterial lysates were boiled and the supernatant, expected to contain alpha-synuclein was analyzed by Western blot with an anti-phospho-S129-alpha-synuclein antibody (11A5), by using the SYPRO Ruby™ and ProZDiamond™ dyes (total protein and phospho-Ser/Thr specific dye respectively), by SDS-PAGE and by mass spectrometry, with the results that a fairly pure phospho-S129-alpha-synuclein product was isolated that, upon analysis by mass spectrometry was revealed to be more than 95% phosphorylated. To ensure that the final product was 100% phosphorylated and highly pure, the supernatant of the last centrifugation was passed through an 11A5-sepharose-affinity purification column one or more times. Any contamination was removed using HPLC.

IV. Agents to Modulate Expression

A number of agents of well-characterized general classes can be used to inhibit expression of any desired gene of known sequence, such as zinc finger proteins, ribozymes, siRNAs and antisense RNAs. Zinc finger proteins can also be used to activate expression of desired genes. Preferably the gene to be inhibited is PLK2 or GRK6 because the kinases encoded by these genes directly phosphorylating alpha-synuclein, and particularly PLK2. APEG1, CDC7L1, MET GRK1, GRK2, GRK6, IKBKB, CKII and GRK7 are also preferred targets for inhibition because they are likely to be indirect activators of the direct kinase(s). PRKG1, MAPK13, and GAK are preferred candidates for activation in Lewy body diseases because they are negative regulators of the phosphorylation of alpha-synuclein. Synphilin is a preferred target for inhibition because, although not a kinase, it is associated with increased phosphorylation of alpha-synuclein (typically in the presence of a kinase such as PLK2).

Zinc finger proteins can be engineered or selected to bind to any desired target site within a kinase gene of known sequence. An exemplary motif characterizing one class of these proteins ($C_2H_2$ class) is -Cys-$(X)_{2-4}$-Cys-$(X)_{12}$-His-$(X)_{3-5}$-His (where X is any amino acid). A single finger domain is about 30 amino acids in length, and several structural studies have demonstrated that it contains an alpha helix containing the two invariant histidine residues and two invariant cysteine residues in a beta turn co-ordinated through zinc. In some methods, the target site is within a promoter or enhancer. In other methods, the target site is within the structural gene. In some methods, the zinc finger protein is linked to a transcriptional repressor, such as the KRAB repression domain from the human KOX-1 protein (Thiesen et al., *New Biologist* 2, 363-374 (1990); Margolin et al., *Proc. Natl. Acad. Sci. USA* 91, 4509-4513 (1994); Pengue et al., *Nucl. Acids Res.* 22:2908-2914 (1994); Witzgall et al., *Proc. Natl. Acad. Sci. USA* 91, 4514-4518 (1994)). In some methods, the zinc finger protein is linked to a transcriptional activator, such as VIP16. Methods for selecting target sites suitable for targeting by zinc finger proteins, and methods for designing zinc finger proteins to bind to selected target sites are described in WO 00/00388. Methods for selecting zinc finger proteins to bind to a target using phage display are described by EP.95908614.1. The target site used for design of a zinc finger protein is typically of the order of 9-19 nucleotides.

Ribozymes are RNA molecules that act as enzymes and can be engineered to cleave other RNA molecules at specific sites. The ribozyme itself is not consumed in this process, and can act catalytically to cleave multiple copies of mRNA target molecules. General rules for the design of ribozymes that cleave target RNA in trans are described in Haseloff & Gerlach, (1988) Nature 334:585-591 and Hollenbeck, (1987) Nature 328:596-603 and U.S. Pat. No. 5,496,698. Ribozymes typically include two flanking segments that show complementarity to and bind to two sites on a transcript (target subsites) of a gene encoding a kinase of the invention and a catalytic region between the flanking segments. The flanking segments are typically 5-9 nucleotides long and optimally 6 to 8 nucleotides long. The catalytic region of the ribozyme is generally about 22 nucleotides in length. The mRNA target contains a consensus cleavage site between the target subsites having the general formula NUN, and preferably GUC. (Kashani-Sabet and Scanlon, (1995) Cancer Gene Therapy 2:213-223; Perriman, et al., (1992) *Gene (Amst)* 113:157-163; Rufflier, et al., (1990) *Biochemistry* 29: 10695-10702); Birikh, et al., (1997) *Eur. J. Biochem.* 245:1-16; Perrealt, et al., (1991) *Biochemistry* 30:4020-4025). The specificity of a ribozyme can be controlled by selection of the target subsites and thus the flanking segments of the ribozyme that are complementary to such subsites. Ribozymes can be delivered either as RNA molecules or in the form of DNA encoding the ribozyme as a component of a replicable vector or in nonreplicable form as described below.

Expression of a target kinase gene can also be reduced by delivering nucleic acids having sequences complementary to the regulatory region of the target gene (i.e., the target gene promoter and/or enhancers) to form triple helical structures which prevent transcription of the target gene in target cells in the body. See generally, Helene, (1991), Anticancer Drug Des., 6(6):569-584; Helene, et al., (1992), *Ann. N.Y. Acad. Sci.*, 60:27-36; and Maher, (1992), *Bioassays* 14(12):807-815.

Antisense polynucleotides can cause suppression by binding to, and interfering with the translation of sense mRNA, interfering with transcription, interfering with processing or localization of RNA precursors, repressing transcription of mRNA or acting through some other mechanism (see, e.g., Sallenger et al. *Nature* 418, 252 (2002). The particular mechanism by which the antisense molecule reduces expression is not critical. Typically antisense polynucleotides comprise a single-stranded antisense sequence of at least 7 to 10 to typically 20 or more nucleotides that specifically hybridize to a sequence from mRNA of a kinase gene of the invention. Some antisense polynucleotides are from about 10 to about 50 nucleotides in length or from about 14 to about 35 nucleotides in length. Some antisense polynucleotides are polynucleotides of less than about 100 nucleotides or less than about 200 nucleotides. In general, the antisense polynucleotide should be long enough to form a stable duplex but short enough, depending on the mode of delivery, to administer in vivo, if desired. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the polynucleotide (e.g., methylphosphonate backbone, peptide nucleic acid, phosphorothioate), among other factors.

siRNAs are relatively short, at least partly double stranded, RNA molecules that serve to inhibit expression of a complementary mRNA transcript, such as a kinase transcript. Although an understanding of mechanism is not required for practice of the invention, it is believed that siRNAs act by inducing degradation of a complementary mRNA transcript. Principles for design and use of siRNAs generally are described by WO 99/32619, Elbashir, EMBO J. 20, 6877-6888 (2001) and Nykanen et al., *Cell* 107, 309-321 (2001); WO 01/29058. siRNAs are formed from two strands of at least partly complementary RNA, each strand preferably of 10-30, 15-25, or 17-23 or 19-21 nucleotides long. The strands can be perfectly complementary to each other throughout their length or can have single stranded 3'-overhangs at one or both ends of an otherwise double stranded molecule. Single stranded overhangs, if present, are usually of 1-6 bases with 1 or 2 bases being preferred. The antisense strand of an siRNA is selected to be substantially complementary (e.g., at least 80, 90, 95% and preferably 100%) complementary to a segment of a transcript from a gene of the invention. Any mismatched bases preferably occur at or near the ends of the strands of the siRNA. Mismatched bases at the ends can be deoxyribonucleotides. The sense strand of an siRNA shows an analogous relationship with the complement of the segment of the gene transcript of interest. siRNAs having two strands, each having 19 bases of perfect complementarity, and having two unmatched bases at the 3' end of the sense strand and one at the 3' end of the antisense strand are particularly suitable.

If an siRNA is to be administered as such, as distinct from the form of DNA encoding the siRNA, then the strands of an siRNA can contain one or more nucleotide analogs. The nucleotide analogs are located at positions at which inhibitor activity is not substantially effected, e.g. in a region at the 5'-end and/or the 3'-end, particularly single stranded overhang regions. Preferred nucleotide analogues are sugar- or backbone-modified ribonucleotides. Nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8 position, e.g. 8-bromo guanosine; deaza nucleotides, e.g. 7-deaza-adenosine; O- and N-alkylated nucleotides, e.g. N6-methyl adenosine are also suitable. In preferred sugar-modified ribonucleotides, the 2' OH-group is replaced by a group selected from H, OR, R, halo, SH, SR, NH2, NHR, NR2 or CN, wherein R is C1-C6 alkyl, alkenyl or alkynyl and halo is F, CI, Br or I. In preferred backbone-modified ribonucleotides the phosphoester group connecting to adjacent ribonucleotides is replaced by a modified group, e.g. of phosphothioate group. A further preferred modification is to introduce a phosphate group on the 5' hydroxide residue of an siRNA. Such a group can be introduced by treatment of an siRNA with ATP and T4 kinase. The phosphodiester linkages of natural RNA can also be modified to include at least one of a nitrogen or sulfur heteroatom. Modifications in RNA structure can be tailored to allow specific genetic inhibition while avoiding a general panic response in some organisms which is generated by dsRNA. Likewise, bases can be modified to block the activity of adenosine deaminase.

V. Identification of Kinase

Kinases that directly or indirectly modulate phosphorylation of alpha-synuclein or its production can be identified as shown in the examples. In general, a library of potential inhibitors is designed based on the known sequences of a collection of kinase genes. The members of the library can be any of the types of molecule described above. Members of the library are then introduced into cells expressing alpha-synuclein. Preferably both the cells and the alpha-synuclein are human. Usually, such cells are transfected with both DNA encoding human alpha-synuclein and DNA encoding the library member to be tested. Library members can be screened individually or en masse. After introduction of a library member, and culturing for a period sufficient for the library member to be expressed and effect repression of its kinase, the levels of total alpha-synuclein and phosphorylated alpha-synuclein are measured and compared with corresponding levels in an otherwise similar control cell not treated with a library member to suppress expression of a kinase. Measurements can be made by immunoassay using an antibody specific for alpha-synuclein (preferably human alpha-synuclein) to measure total levels of alpha-synuclein, and an antibody specific for phosphorylated alpha-synuclein to measure the level of phosphorylated alpha-synuclein. Exemplary antibodies are described in PCT/US2004/037444 filed Nov. 8, 2004 (incorporated by reference). A reduction in level of phosphorylated alpha-synuclein between the treated and control cell that is significant in the sense of being outside the typical margin of error for measurements, signals that the inhibitor introduced into the cell inhibited a kinase, which directly or indirectly affected phosphorylation of alpha-synuclein. The identity of the kinase can be determined from the identity of inhibitor, either by screening inhibitors individually, or if inhibitors are screened en masse, by sequencing the nucleic acid encoding the inhibitor. Likewise a reduction in the total level of alpha-synuclein between treated and control cells that is outside the margin of typical experimental error in measuring such levels provides an indication that the inhibitor inhibits a kinase that indirectly affects the expression level of alpha-synuclein.

Kinases identified by the initial screen, particularly, kinases known to be serine kinases, can then be tested for their capacity to phosphorylate alpha-synuclein in vitro, in cells or in transgenic animal models. An in vitro assay is an indication of whether a kinase directly phosphorylates alpha-synuclein and is therefore only useful for the kinases identified in the initial screen which are thought to be capable of directly phosphorylating alpha-synuclein. Cellular and transgenic assays can be used to screen kinases that affect phosphorylation either directly or indirectly. In vitro assays are performed by contacting alpha-synuclein with the kinase under test, ATP and in a suitable buffer. Preferably, the ATP is γ-32P ATP, in which case phosphorylated alpha-synuclein is radiolabeled and can be detected on a gel. Phosphorylation can also be measured using an antibody specific to phosphorylated alpha-synuclein as described before. Alternatively, phosphorylation can be measured indirectly by measuring ATP consumption using a coupled assay, in which ADP is detected as described for example by Nature 78,632 (1956); Mol. Pharmacol. 6, 31-40 (1970). The extent of phosphorylation can be compared with a control in which the kinase or ATP or both is/are omitted. An increase in phosphorylation is an indication that the kinase directly phosphorylates alpha-synuclein. Cellular assays are performed on cells expressing alpha-synuclein, preferably human alpha-synuclein transfected into the cells. A nucleic acid capable of expressing the kinase is also transfected into the cells. The level of phosphorylated alpha-synuclein in the cells is measured relative to that in similar control cells lacking the transfected kinase. An increase in phosphorylation is an indication that the kinase directly or indirectly phosphorylates alpha-synuclein. Transgenic assays can be performed by comparing a transgenic animal expressing human alpha-synuclein disposed to develop Lewy body-like deposits with a similar animal also expressing a kinase transgene. A reduction in phosphorylated alpha-synuclein and/or in Lewy body-like deposits in the transgenic animal with the additional kinase transgene relative to the transgenic animal with just the alpha-synuclein transgene is an indication that the kinase is directly or indirectly involved in phosphorylating alpha-synuclein.

VI Compounds to Modulate Activity

A variety of compounds can be screened for capacity to modulate (usually inhibit) expression or activity of kinases. PLK2 or GRK6 are preferred kinases for inhibition because they are candidates for directly phosphorylating alpha-synuclein. PLK2 is a particularly preferred kinase because it has been shown to phosphorylate alpha-synuclein to a much higher level than GRK6 or other kinases tested herein. APEG1, CDC7L1, MET GRK1, GRK2, GRK6, IKBKB, CKII and GRK7 are also preferred kinases for inhibition because they are likely to be indirect activators of the direct kinase(s). PRKG1, MAPK13, and GAK are preferred kinases for activation in Lewy body diseases because they are negative regulators of the phosphorylation of alpha-synuclein. Alternatively, these kinases themselves or fragments or mimetics thereof having similar activity can be used directly as inhibitors of alpha-synuclein phosphorylation. Synuclein can be used as an alternative therapeutic target for inhibition of alpha-synuclein phosphorylation. For example, synphilin can be added to an assay having alpha-synuclein and PLK-2 expression and inhibitors of synphilin identified.

The compounds to be screened for capacity to modulate expression or activity of kinases include the modulators of expression described in section IV. These compounds also include many known examples of kinase inhibitors, some of which are already approved for therapeutic uses or in clinical trials usually for treatment of cancer. Lead structures include quinazolines, pyrido[d]- and pyrimidol[d]pyrimidines, pyrazolo[d]-pyrimidienes, pyrrolo[d]pyrimidines, pheylamino-pyrimidines, 1-oxo-3-aryl-1H-indene-2-carboxylic acid derivatives, and substituted indolin-2-ones and natural products such as strauosporine (see Traxler et al., Medicinal Research Reviews 21, 499-512 (2001)). Some such compounds are commercially available from Calbiochem-Novabiochem Corp. (La Jolla, Calif.) including H89, Y27632, AT877 (fasudil hydrochloride), rottlerin, KN62, U0123, PD184352, PD98059, SB203580, SB202190, wortmannin, Li$^+$, Ro 318220, chelerythrein and 10-[3-(1-piperazinyl)propyl]-2-trifluoromethyl-phenothiazine (see Davies, Biochem. J. 351, 95-105 (2000)). Other compounds currently in clinical trials include ST1571 (GlivecTM, a phenylamino-pyrimidine derivative) (Novartis), ZD1839 (Iressa) (AstraZeneca), OSI-774 (Roche/OSI), PKI166 (Novartis), CI1033 (Pfizer/Warner-Lambert), EKB-569 (Wyeth-Ayerst), SU5416 (SUGEN), PTK787/ZK224584, aniline-phthalazine derivative (Novartis/Schering AG), SU6668 (Sugen), ZD6474 (AstraZeneca), and CEP2583 (Cephalon). Caveolin-1 is an example of a compound known to modulate the activity of the GRK kinases. Examples of compounds known to modulate the activity of the PLK2/SNK kinases include the RING-H2 domain of hVPS18 (human vacuolar protein sorting 18), and calcium- and integrin-binding protein CIB. Other compounds can be obtained from natural sources, such as, e.g., marine microorganisms, algae, plants, and fungi. Other compounds that can be tested include compounds known to interact with alpha-synuclein, such as synphilin. Alternatively, compounds can be from combinatorial libraries of agents, including peptides or small molecules, or from existing repertoires of chemical compounds synthesized in industry, e.g., by the chemical, pharmaceutical, environmental, agricultural, marine, cosmeceutical, drug, and biotechnological industries. Compounds can include, e.g., pharmaceuticals, therapeutics, environmental, agricultural, or industrial agents, pollutants, cosmeceuticals, drugs, organic compounds, lipids, glucocorticoids, antibiotics, peptides, proteins, sugars, carbohydrates, and chimeric molecules.

Combinatorial libraries can be produced for many types of compounds that can be synthesized in a step-by-step fashion. Such compounds include polypeptides, proteins, nucleic acids, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of compounds can be constructed by the encoded synthetic libraries (ESL) method described in Affymax, WO 95/12608, Affymax WO 93/06121, Columbia University, WO 94/08051, Pharmacopeia, WO 95/35503 and Scripps, WO 95/30642 (each of which is incorporated herein by reference in its entirety for all purposes). Peptide libraries can also be generated by phage display methods. See, e.g., Devlin, WO 91/18980. Compounds to be screened can also be obtained from governmental or private sources, including, e.g., the National Cancer Institute's (NCI) Natural Product Repository, Bethesda, Md., the NCI Open Synthetic Compound Collection, Bethesda, Md., NCI's Developmental Therapeutics Program, or the like.

The compounds include antibodies, both intact and binding fragments thereof, such as Fabs, Fvs, which specifically bind to a kinase of the invention. Usually the antibody is a monoclonal antibody although polyclonal antibodies can also be expressed recombinantly (see, e.g., U.S. Pat. No. 6,555, 310). Examples of antibodies that can be expressed include mouse antibodies, chimeric antibodies, humanized antibodies, veneered antibodies and human antibodies. Chimeric antibodies are antibodies whose light and heavy chain genes have been constructed, typically by genetic engineering, from immunoglobulin gene segments belonging to different species (see, e.g., Boyce et al., Annals of Oncology 14:520-535 (2003)). For example, the variable (V) segments of the genes from a mouse monoclonal antibody may be joined to human constant (C) segments. A typical chimeric antibody is thus a hybrid protein consisting of the V or antigen-binding domain from a mouse antibody and the C or effector domain from a human antibody. Humanized antibodies have variable region framework residues substantially from a human antibody (termed an acceptor antibody) and complementarity determining regions substantially from a mouse-antibody, (referred to as the donor immunoglobulin). See Queen et al., Proc. Natl. Acad. Sci. USA 86:10029-10033 (1989) and WO 90/07861, U.S. Pat. Nos. 5,693,762, 5,693,761, 5,585,089, 5,530,101 and Winter, U.S. Pat. No. 5,225,539. The constant region(s), if present, are also substantially or entirely from a human immunoglobulin. Antibodies can be obtained by conventional hybridoma approaches, phage display (see, e.g., Dower et al., WO 91/17271 and McCafferty et al., WO 92/01047), use of transgenic mice with human immune systems (Lonberg et al., WO93/12227 (1993)), among other sources. Nucleic acids encoding immunoglobulin chains can be obtained from hybridomas or cell lines producing antibodies, or based on immunoglobulin nucleic acid or amino acid sequences in the published literature.

VII. Transgenic Animal Models of Lewy Body Disease

Transgenic animal models are useful for testing the capacity of kinases to effect phosphorylation of alpha-synuclein and formation of Lewy-like bodies as described above. Transgenic animals are also useful for screening agents for activity in modulating phosphorylation or production of alpha-synuclein. Particularly preferred are agents that inhibit or are suspected of inhibiting kinases include PLK2 and GRK6, or APEG1, CDC7L1, MET GRK1, GRK2, GRK6, IKBKB, CKII and GRK7. Also preferred are agents that activate or are suspected of activating kinases PRKG1, MAPK13, and GAK. Further, knockout animals (i.e., animals in which an endogenous kinase is inactivated either by insertional inactivation or trans inhibition by an siRNA, zinc finger protein or the like) are useful for identifying the effect of eliminating activity of a kinase on an animal. For example, analysis of a PLK2-knockout mouse can indicate whether inhibitors of PLK2 have any side effects. Analogous knockouts can reveal similar information for other kinases.

In general, transgenic models have a genome comprising an alpha-synuclein transgene in operable linkage with one or more regulatory sequences to ensure its expression. Expression of the transgene leads to Lewy-body like deposits of alpha-synuclein in the brain of the animal. Several such transgenic animals have been described in the scientific and patent literature (see Masliah et al, Am. J. Pathol. (1996) 148:201-10 and Feany et al., Nature (2000) 404:394-8)), U.S. Pat. No. 5,811,633 (for transgenic animals with a mutant form of APP). Some transgenic animals express variant or mutant alpha-synuclein, such as familial mutants A30P, A53T, and E46K of alpha synuclein. Some transgenic animals have an additional transgene, such as a transgene encoding a kinase as described above. Transgenic animals bearing a transgene expressing alpha-synuclein protein can also be crossed with other transgenic models of neurogenic disease, such as models of Alzheimer's disease. For example, transgenic animals bearing a transgene expressing a truncated alpha-synuclein protein can be crossed with transgenic animals bearing a transgene expressed APP with a FAD mutation as described by e.g., Games et al., Nature 373, 523 (1995) McConlogue et al., U.S. Pat. No. 5,612,486, Hsiao et al., Science 274, 99 (1996); Staufenbiel et al., Proc. Natl. Acad. Sci. USA 94, 13287-13292 (1997); Sturchler-Pierrat et al., Proc. Natl. Acad. Sci. USA 94, 13287-13292 (1997); Borchelt et al., Neuron 19, 939-945 (1997)). The procedure for performing such a cross is described by e.g., Masliah et al., PNAS USA 98:12245-12250 (2001), which reports a cross between transgenic mice expressing a full length alpha-synuclein with PDAPP mice as described by Games et al Transgenic animals of the invention are preferably rodents, such as mice or rats, or insects, such as Drosophila. Transgenic animals can be produced by introduction of a transgene at the germline stage in which case all or substantially all (except for rare loss through somatic mutation) of the cells of the transgenic animal include the transgene integrated into the genome. Transgenes can be introduced by microinjection, nuclear transfer or viral infection into cells or animals. Lentiviruses are particularly suitable for the latter. Alternatively, transgenes can be introduced by viral infection into the brain of the animal. Such transgenes are not part of the germline of recipient animals but can be targeted to regions of the brain responsible for disease (e.g., the substantia nigra). Such animal models incorporate an alpha-synuclein into the genome of brain cells and are disposed to develop at least one characteristic of LBD disease. Lentiviruses provide a suitable vehicle for so introducing an alpha-synuclein transgene into the brain (see Brain Pathology 13, 364-372 (2003); Bjorklund, Trends Neurosci. 26, 386-92 (2003), Lotharius et al., J. Biol. Chem. 277, 38884-94 (2002), Zhou et al., Brain Research 866, 33-43 (2000)). Transgenic animals can also include a transgene capable of expressing one of the kinases of the invention (e.g., a nucleic acid encoding the kinase in operable linkage with regulatory elements to ensure its expression in the brain of an animal), instead of or as well as a transgene expressing alpha synuclein. Optionally, a transgene expressing synphilin can be included as well.

Cellular models of Lewy body disease can also be used in the screening methods of the invention. Cells transfected with alpha-synuclein form inclusion bodies containing aggregated alpha-synuclein. The transformed cells are preferably neuronal cells, such as GT1-7 neuronal cells (Hsue et al. Am. J. Pathol. 157:401-410 (2000)), PC 12 cells or SY5Y neuroblastoma cells. PEAK and/or HCC cells can also be used (see example 11). The cells are preferably human cells. A vector comprising a segment encoding a form of alpha-synuclein operably linked to one or more regulatory sequences that ensure expression of the expression is transfected into the cells. Cells can also be transfected with a nucleic acid encoding a kinase of the invention as described above. Transfected cells can be used to screen agents for activity in clearing alpha-synuclein inclusions. An exemplary cellular model is identified in Example 11 in which HCC neuronal cells are transfected with synuclein and PLK2 with the result that aggregation and phosphorylation of the synuclein matching LB formation occurs. In order to identify inhibitors of the kinase, the inhibitor is expressed with the synuclein and PLK2 and a reduction in the amount of Phosphorylation and/or aggregation is identified.

VIII. Identification of Modulators

Agents that modulate expression or activity of a kinase that directly or indirectly phosphorylates alpha-synuclein can be identified by a variety of assays. Particularly preferred are agents that inhibit kinases PLK2 or GRK6, or APEG1, CDC7L1, MET GRK1, GRK2, GRK6, IKBKB, CKII and GRK7, or agents that activate PRKG1, MAPK13, and GAK. Agents that modulate expression can be identified in cell-based assays in which an agent under test is introduced into a cell expressing alpha-synuclein and a kinase that directly or indirectly effects phosphorylation of the alpha-synuclein or modulates levels of total alpha-synuclein. Optionally, particularly for PLK2, synphilin can be expressed as well to augment activity of the kinase. The agent can be introduced directly or in the form of a nucleic acid encoding the agent and capable of expressing the agent. The cell can naturally express the alpha-synuclein and kinase or one or both of these can be introduced into the cell by transfection of a suitable nucleic acid. The effect of the agent on expression of the kinase can be measured directly from the level of the kinase or its mRNA, or indirectly by measuring the level of phosphorylated alpha-synuclein or total alpha-synuclein as described above. The level of kinase mRNA can be assayed by a hybridization type assay. The level of the kinase can be assayed by an immunoassay. Optionally, the kinase is tagged with a peptide label such as Flag™ (Hopp et al., BioTechnology 6, 1204-1210 (1988)) to facilitate detection. An agent that decrease the level of the kinase, decrease the level of phosphorylation of alpha-synuclein and/or decrease the level of total alpha-synuclein relative to similar control cells not treated with an agent have a pharmacological activity potentially useful for treatment of Lewy body diseases.

Agents are also screened for activity to modulate activity of a kinase suspected of phosphorylating alpha-synuclein or increasing total levels of alpha-synuclein. An initial screen can be performed to select a subset of agents capable of specifically binding to a kinase. Such an assay can be performed in vitro using an isolated kinase or fragment thereof having kinase activity.

Agents identified by such a screen can then be assayed functionally. Agents can also be directly assayed functionally without the binding assay. For a kinase that directly phosphorylates alpha-synuclein, modulators can be screened by an in vitro assay combining the kinase, alpha-synuclein, ATP and the modulator in comparison with a control in which the modulator is omitted. Optionally, synphilin can be included as well to increase phosphorylation particularly if the kinase is PLK2. The modulator has potentially useful pharmacological activity if it reduces the level of phosphorylation beyond the margin of typical experimental error relative to the control.

Agents can also be screened in cells expressing alpha-synuclein and the kinase under test, and optionally, particularly if the kinase is PLK2, synphilin. Such screens are effective regardless of whether the kinase phosphorylates alpha-synuclein directly or indirectly, or otherwise affects levels of alpha-synuclein. Cells are contacted with the agent and levels of total alpha-synuclein and phosphorylated alpha-synuclein are measured, as above, relative to a control cell not treated with the agent. A reduction in the level of phosphorylated alpha-synuclein or total alpha-synuclein relative to the corresponding level in a control cell not treated with the agent, beyond the margin of typical experimental error, is an indication that the compound has pharmacological activity potential useful in treating Lewy body diseases.

Agents can also be screened in transgenic animal models of Lewy body disease, alone or in combination with the other assays described above. Total levels of alpha-synuclein, phosphorylated alpha-synuclein or Lewy-like bodies or other indica of Lewy Body pathology or symptoms are measured in a transgenic animal treated with an agent under test relative to corresponding levels in a similar control animal not treated with the agent. A reduction in one or more of these levels is an indication, the agent has pharmacological activity potentially useful in treating Lewy body diseases.

The kinase used in the above assays and cellular and transgenic models is preferably a human kinase having a sequence in one of the references or accession numbers provided in this application. However, allelic (variants within a species) and species variants (variants between specis) of such a kinase can also be used, as can variants having at least 90% sequence identity to such a kinase. For subsequent clinical use, agents identified by such assays are capable of modulating the activity or expression of a natural kinase, preferably a form occurring in humans.

IX. Lewy Body Diseases

Lewy Body Diseases (LBD) are characterized by degeneration of the dopaminergic system, motor alterations, cognitive impairment, and formation of Lewy bodies (LBs). (McKeith et al., *Clinical and pathological diagnosis of dementia with Lewy bodies (DLB): Report of the CDLB International Workshop, Neurology* (1996) 47:1113-24). Lewy Bodies are spherical protein deposits found in nerve cells. Their presence in the brain disrupts the brain's normal function interrupting the action of chemical messengers including acetylcholine and dopamine. Lewy Body diseases include Parkinson's disease (including idiopathic Parkinson's disease(PD)), Diffuse Lewy Body Disease (DLBD) also known as Dementia with Lewy Bodies (DLB), Combined Alzheimer's and Parkinson disease and multiple system atrophy (MSA). DLBD shares symptoms of both Alzheimer's and Parkinson's disease. DLBD differs from Parkinson's disease mainly in the location of Lewy Bodies. In DLBD Lewy Bodies form mainly in the cortex. In Parkinson's disease, they form mainly in the substantia nigra. Other Lewy Body diseases include Pure Autonomic Failure, Lewy body dysphagia, Incidental LBD, Inherited LBD (e.g., mutations of the alpha-synuclein gene, PARK3 and PARK4) and Multiple System Atrophy (e.g., Olivopontocerebellar Atrophy, Striatonigral Degeneration and Shy-Drager Syndrome).

X. Methods of Treatment

The invention provides several methods of preventing or treating Lewy Body disease in patients suffering from or at risk of such disease. Therapeutic agents include any of the agents described above that inhibit phosphorylation of alpha-synuclein and/or reduce total levels of alpha-synuclein.

Patients amenable to treatment include individuals at risk of disease of a LBD but not showing symptoms, as well as patients presently showing symptoms. Therefore, the present methods can be administered prophylactically to individuals who have a known genetic risk of a LBD. Such individuals include those having relatives who have experienced this disease, and those whose risk is determined by analysis of genetic or biochemical markers. Genetic markers of risk toward PD include mutations in the alpha-synuclein or Parkin, UCHLI, LRRK2, and CYP2D6 genes; particularly mutations at positions 30 and 53 of the alpha-synuclein gene. Another genetic marker of risk toward PD includes measuring the levels or SNCA dosage or transcription. Individuals presently suffering from Parkinson's disease can be recognized from its clinical manifestations including resting tremor, muscular rigidity, bradykinesia and postural instability.

In some methods, the patient is free of clinical symptoms or risk factors for any amyloidogenic disease other than one characterized by Lewy bodies. In some methods, the patient is free of clinical symptoms or risk factors of any disease characterized by extracellular amyloid deposits.

Treatment typically entails multiple dosages over a period of time. Treatment can be monitored by assaying signs or symptoms of the disease being treated relative to base line measurements before initiating treatment. In some methods, administration of an agent results in reduction of intracellular levels of aggregated alpha-synuclein. In some methods, administration of the agent results in a reduction in levels phosphorylated. In some methods, administration of an agent results in improvement in a clinical symptom of a LBD, such as motor or cognitive function in the case of Parkinson's disease.

In prophylactic applications, pharmaceutical compositions or medicaments are administered to a patient susceptible to, or otherwise at risk of a LBD in regime comprising an amount and frequency of administration of the composition or medicament sufficient to eliminate or reduce the risk, lessen the severity, or delay the outset of the disease, including physiological, biochemical, histologic and/or behavioral symptoms of the disease, its complications and intermediate pathological phenotypes presenting during development of the disease. In therapeutic applications, compositions or medicates are administered to a patient suspected of, or already suffering from such a disease in a regime comprising an amount and frequency of administration of the composition sufficient to cure, or at least partially arrest, the symptoms of the disease (physiological, biochemical, histologic and/or behavioral), including its complications and intermediate pathological phenotypes in development of the disease. An amount adequate to accomplish therapeutic or prophylactic treatment is defined as a therapeutically- or prophylactically-effective dose. A combination of amount and dosage frequency adequate to accomplish therapeutic or prophylactic treatment is defined as a therapeutically or prophylatically-effective regime.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

The dosage and frequency of administration can vary depending on whether the treatment is prophylactic or therapeutic. Guidance can be obtained from the dosing schedules of kinase inhibitors currently approved or in clinical trials for other indications. Dosages in the range of 0.1-1000 mg, preferably 10-500 mg. Frequency of dosing (e.g., daily, weekly or monthly) depends on the half-life of the drug. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Therapeutic agents can be administered by parenteral, topical, intravenous, oral, subcutaneous, intraarterial, intracranial, intrathecal, intraperitoneal, intranasal or intramuscular means for prophylactic and/or therapeutic treatment. In some methods, agents are injected directly into a particular tissue where deposits have accumulated, for example intracranial injection. In some methods, agents are administered as a sustained release composition or device, such as a Medi-pad™ device. Small molecules that pass through the blood brain barrier sufficiently are usually administered orally, but can also be administered intravenously.

Agents of the invention can optionally be administered in combination with other agents that are at least partly effective in treatment of LBD. Agents of the invention can also be administered in conjunction with other agents that increase passage of the agents of the invention across the blood-brain barrier.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose(TM), agarose, cellulose, and the like), polymeric amino acids, amino acid copolymers, and lipid aggregates (such as oil droplets or liposomes).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl. Compositions for parenteral administration are typically substantially sterile, substantially isotonic and manufactured under GMP conditions of the FDA or similar body.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249, 1527 (1990) and Hanes, *Advanced Drug Delivery Reviews* 28, 97-119 (1997). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein. Alternatively, transdermal delivery can be achieved using a skin path or using transferosomes (Paul et al., *Eur. J. Immunol.* 25, 3521-24 (1995); Cevc et al., *Biochem. Biophys. Acta* 1368, 201-15 (1998)).

In the following examples, transfection of cells with siRNA and knockdown of specific kinase targets was employed to identify kinases that modulated alpha-synuclein phosphorylation directly or indirectly. Subsequent experiments in vitro and in tissue culture showed that two of these kinases, PLK2 and GRK6 directly and specifically phosphorylated the Serine 129 of alpha-synuclein. Further experiments showed that PLK2 phosphorylated the Serine 129 of alpha-synuclein to a much greater extent than GRK6 and other kinases described herein. Thus, PLK2 is very likely a synuclein kinase.

EXAMPLES

Example 1

Screen for Kinases that Modulate Alpha-Synuclein Phosphorylation

To identify the kinase or kinases that phosphorylates α-synuclein at Serine 129 an siRNA kinase library (Ambion) was screened on cells containing a quantifiable amount of phosphorylated α-synuclein. Human embryonic kidney cell line HEK293 cells (PEAK cells) stably transfected with human wild-type α-synuclein under control of a CMV promoter (PEAK-Syn cells) were transfected with 100 nM siRNAs targeting 597 human kinases and were assayed by ELISA assays to quantitate total and phospho-synuclein levels. Ninety-five kinases with siRNAs that altered the percentage of phosphorylated alpha-synuclein were identified (see Tables 1-3). Of those, 28 belonged to the class of kinases that phosphorylate serine residues and hence were capable of directly phosphorylating α-synuclein at Serine 129. Others were tyrosine kinases. Although tyrosine kinases do not phosphorylate α-synuclein at ser-129 directly, they can act as upstream regulators of the alpha-synuclein kinase. Two of these ser/thr kinases, casein kinase 2 and calcium/calmodulin dependent protein kinase II, have been reported to phosphorylate α-synuclein in vitro (Pronin et al, J. Biol. Chem. 275: 26515-26522 (2000), Okochoa et al, J. Biol. Chem. 275: 390-397 (2000); Nakajo et al, Eur. J. Biochem. 217: 1057-1063 (1993) and a casein kinase 2 inhibitor has been reported to increase phospho-synuclein levels in cells (Okochoa et al, 2000). Several of the GRK family members (although not GRK6) have been reported to phosphorylate alpha-synuclein in vitro (Pronin et al, 2000). GRK2 expression in flies has been reported to increase phospho-synuclein levels (Chen and Feany, Nature Neurosci. 8: 657-663 (2005)).

In addition to kinases that lower phospho-synuclein levels, 99 kinases whose siRNAs altered total α-synuclein levels in the PEAK-Syn cells were identified in Table 2 and included fucokinase (FUK), genbank number NM_145059; Protein Kinase N1 (PRKCL1, PKN1), genbank number NM_002741; Doublecortin and CaM kinase-like 1 (DCAMKL1) NM_004734; Branched chain Ketoacid dehydrogenase kinase (BCKDK) NM_005881; Aurora Kinase C (AURKC, STK13); NM_003160, Kinase suppressor of ras 2 (FLJ25965), NM_173598; FLJ32704; MAP2K6; and Tousled-like kinase 2 (TLK2) NM_006842. The mechanism of action may involve either regulation of alpha-synuclein turnover or synthesis (See Table 3).

Tables 1A, 1B and 1C show kinases whose inhibition modulates the phosphorylation at position ser-129. The normal type at the top of each table shows kinases for which phosphorylation is reduced when expression of the kinase is inhibited, and those in shaded type at the bottom of each table show kinases for which phosphorylation is increased when the kinase is inhibited. Table 1A, B, and C differ in the type of kinase. Table 1A shows kinases that can phosphorylate serine residues and often tyrosine and/or threonine as well. Table 1B shows tyrosine kinases that cannot (so far as is known) modify serine residues. Table 1C shows proteins not known to have kinase activity. Kinases from the upper portion of Table 1A are candidates for direct phosphorylation of ser-129 of alpha-synuclein. Kinases from the upper part of Table 1B are also useful therapeutic targets via roles indirectly phosphorylating alpha-synuclein. Proteins in the upper part of Table 1C are also useful therapeutic targets for the same reason. Cols. 1, 2 and 3 of each table indicate the gene name, kinase name and Genbank accession number of kinases. The next column indicates whether inhibition of the kinase decreased ("down") or increased ("up") phosphorylation. The next three columns indicate the number of standard deviations the measured level of phosphorylation departs from the mean in three independent experiments. The final two columns indicate the kinase family (i.e., amino acid specificity) and group.

Tables 2 and 3 show kinases whose inhibition modulates the overall levels of human alpha-synuclein without changing the percentage of phosphorylation. Table 2 shows all of the kinases with the strongest reduction in levels of human alpha-synuclein. The columns are labeled similarly to Tables 1A, 1B and 1C.

Tables 1A-C: Complete list of Kinase candidates that reduce phosphorylation

TABLE 1A

Serine/Threonine Kinases

| Gene Name | Kinase Name | Genbank | Up/Down | # of SD | # of SD | # of SD | Kinase Family | Kinase Group |
|---|---|---|---|---|---|---|---|---|
| GPRK6 | G protein-coupled receptor kinase 6 | NM_002082 | Down | 1.25 | 1.25 | | Ser/Thr | AGC |
| PDPK1 | 3-Phosphoinositide dependent protein kinase-1 | NM_002613 | Down | 2.25 | 2.75 | | Ser/Thr | AGC |
| FLJ11159 | RIO kinase 2 (yeast) | NM_018343 | Down | 1.5 | 1.5 | | Ser/Thr | Atypical |
| *APEG1 | Aortic preferentially expressed gene 1 | NM_005876 | Down | 1.75 | 2 | 2.25 | Ser/Thr/Tyr | CAMK |
| ARK5 | AMP-activated protein kinase family member 5 | NM_014840 | Down | 1 | 1 | 1.5 | Ser/Thr | CAMK |
| *CAMK1 | Calcium/calmodulin-dependent protein kinase I | NM_003656 | Down | 1.5 | 1.75 | 2 | Ser/Thr | CAMK |
| SSTK | Serine/threonine protein kinase SSTK | NM_032037 | Down | 1 | 1 | | Ser/Thr | CAMK |
| PHKG2 | Phosphorylase kinase, gamma 2 (testis) | NM_000294 | Down | 1 | 2 | | Ser/Thr | CAMK |
| CASK | Calcium/calmodulin-dependent serine protein kinase | NM_003688 | Down | 1.25 | 1.25 | | Ser/Thr | CAMK |
| PRKAA2 | Protein kinase, AMP-activated, alpha 2 catalytic subunit | NM_006252 | Down | 1 | 1.75 | | Ser/Thr | CAMK |
| CDK8 | Cyclin-dependent kinase 8 | NM_001260 | Down | 1 | 1 | 1.25 | Ser/Thr | CMGC |
| *CDC2L5 | Cell division cycle 2-like 5 | NM_003718 | Down | 1.25 | 1.5 | | Ser/Thr/Tyr | CMGC |
| ERK8 | Extracellular signal-regulated kinase 8 | NM_139021 | Down | 1.5 | 1.5 | | Ser/Thr | CMGC |
| *CDK4 | Cyclin-dependent kinase 4 | NM_000075 | Down | 1 | 1 | | Ser/Thr** | CMGC |
| CLK3 | CDC-like kinase 3 | NM_003992 | Down | 1 | 1.5 | | Ser/Thr/Tyr | CMGC |
| PRP4 | Pre-mRNA processing factor 4 homolog B (yeast) | NM_003913 | Down | 1.25 | 1.75 | | Ser/Thr | GO |
| CKIIA2 | Casein kinase 2, alpha prime subunit | NM_001896 | Down | 1 | 1.5 | | Ser/Thr | Other |
| PLKII/SNK | Polo like kinase 2 | NM_006622 | Down | 1 | 1.5 | 2.25 | Ser/Thr | Other |
| CKIIA1 | Casein kinase 2, alpha subunit | NM_001895 | Down | 1 | 1.75 | 2.25 | Ser/Thr | Other |
| MAP2K1 | mitogen-activated protein kinase kinase 1 (MEK1; MKK1) | NM_002755 | Down | 1 | 1.75 | | Ser/Thr/Tyr | STE |
| MAP2K4 | mitogen-activated protein kinase kinase 4 (MEK4; MKK4; JNKK) | NM_003010 | Down | 1 | 2 | | Ser/Thr/Tyr | STE |
| MAP2K5 | mitogen-activated protein kinase kinase 5 (MEK5; MKK5) | NM_002757 | Down | 1 | 1.25 | | Ser/Thr/Tyr | STE |
| TESK2 | testis-specific kinase 2 | NM_007170 | Down | 1 | 1 | 1.5 | Ser/Thr/Tyr | TKL |
| RIPK3 | receptor-interacting serine-threonine kinase 3 | NM_006871 | Down | 1 | 1.25 | | Ser/Thr/Tyr | TKL |
| PRKG2 | protein kinase, cGMP-dependent, type II | NM_006259 | Down | 2.25 | | | Ser/Thr | AGC |
| JIK | TAO Kinase 3 (MAP3K18) | NM_016281 | Down | 2 | | | Ser/Thr | STE |
| PAK6 | p21(CDKN1A)-activated kinase 6 | NM_020168 | Down | 2.5 | | | Ser/Thr | STE |
| *CAMK2D | Calcium/calmodulin-dependent protein kinase II-delta | NM_001221 | Down | 1.25 | 1.5 | 2 | Ser/Thr | CAMK |

TABLE 1A-continued

Serine/Threonine Kinases

| Gene Name | Kinase Name | Genbank | Up/Down | # of SD | # of SD | # of SD | Kinase Family | Kinase Group |
|---|---|---|---|---|---|---|---|---|
| *CDC7L1 | CDC7 cell division cycle 7-like 1 | NM_003503 | Down | 1.25 | 2 | 3 | Ser/Thr | Other |
| CDK5 | Cyclin-dependent kinase 5 | NM_004935 | Up | 1 | 1 | 1.25 | Ser/Thr | CMGC |
| PRKWNK1 | Protein kinase, lysine deficient 1 | NM_018979 | Up | 1 | 1.5 | 6.25 | Ser/Thr | Other |
| CDC42BPB | CDC42 binding protein kinase beta (DMPK-like) | NM_006035 | Up | 2.5 | 3.75 | | Ser/Thr | AGC |
| PRKCI | protein kinase C, iota | NM_002740 | Up | 1 | 1.75 | | Ser/Thr | AGC |
| PRKG1 | Protein kinase, cGMP-dependent, regulatory, Type I | NM_006258 | Up | 1 | 1.25 | | Ser/Thr | AGC |
| SMG1 | PI3-kinase-related kinase SMG1 | NM_015092 | Up | 1.25 | 1.5 | | Ser/Thr | Atypical |
| *BRD3 | Bromodomain-containing protein 3 | NM_007371 | Up | 1.25 | 1.75 | | Ser/Thr | Atypical |
| DAPK1 | Death-associated protein kinase 1 | NM_004938 | Up | 1 | 1.25 | 1.25 | Ser/Thr | CAMK |
| PASK | PAS domain containing serine/threonine kinase | NM_015148 | Up | 1 | 1 | | Ser/Thr | CAMK |
| LOC283629 | Chromosome 14 open reading frame 20; Testis-specific serine kinase 4 | NM_174944 | Up | 1 | 1.25 | | Ser/Thr/Tyr | CAMK |
| CDC2 | Cell division cycle 2, G1 to S and G2 to M | NM_001786 | Up | 1.25 | 2.75 | | Ser/Thr/Tyr | CMGC |
| MAPK13 | Mitogen-activated protein kinase 13 | NM_002754 | Up | 1 | 1.25 | 1.75 | Ser/Thr/Tyr | CMGC |
| STK35 | Serine/threonine kinase 35, Clik1 | NM_080836 | Up | 1 | 1.25 | 1.5 | Ser/Thr | Other |
| GAK | Cyclin G associated kinase | NM_005255 | Up | 1 | 1.25 | 1.75 | Ser/Thr | Other |
| ANKRD3 | ankyrin repeat domain 3 | NM_020639 | Up | 1 | 1.75 | | Ser/Thr/Tyr | TKL |
| IRAK3 | Interleukin-1 receptor-associated kinase 3 | NM_007199 | Up | 1.5 | 1.75 | | Ser/Thr | TKL |
| LIMK2 | LIM domain kinase 2 | NM_005569 | Up | 1 | 2 | | Ser/Thr/Tyr | TKL |
| PKMYT1 | Protein kinase, membrane-associated, tyrosine/threonine 1 | NM_004203 | Both | 1.25 | 1.5 | 1.75 | Ser/Thr/Tyr | Other |
| ADRBK2 | adrenergic, beta, receptor kinase 2 (GRK3; BARK2) | NM_005160 | Up | 2 | | | Ser/Thr | AGC |
| AKT3 | v-akt murine thymoma viral oncogene homolog 3 (protein kinase B, gamma) | NM_005465 | Up | 2 | | | Ser/Thr | AGC |
| CDK10 | cyclin-dependent kinase (CDC2-like) 10 | NM_003674 | Up | 5.75 | | | Ser/Thr/Tyr | CMGC |
| EIF2AK3 | eukaryotic translation initiation factor 2-alpha kinase 3 | NM_004836 | Up | 2.5 | | | Ser/Thr | Other |
| BIKE | BMP2 inducible kinase (BMP2K), transcript variant | NM_017593 | Up | 6 | | | Ser/Thr | Other |
| IKBKE | inhibitor of kappa light polypeptide gene enhancer in B-cells, kinase epsilon | NM_014002 | Up | 2 | | | Ser/Thr | Other |
| SDCCAG43 | serologically defined colon cancer antigen 43 | NM_006648 | Up | 4.25 | | | Ser/Thr/Tyr | Other |
| FLJ10074 | SCY1-like 2 (S. cerevisiae) | NM_017988 | Up | 2.25 | | | Ser/Thr | Other |
| FLJ32685 | hypothetical protein FLJ32685 | NM_152534 | Up | 3 | | | Ser/Thr/Tyr | Other |
| NEK11 | NIMA (never in mitosis gene a)-related kinase 11 | NM_024800 | Up | 4 | | | Ser/Thr/Tyr | Other |
| TTK | TTK protein kinase | NM_003318 | Up | 2.5 | | | Ser/Thr/Tyr | Other |

TABLE 1B

Tyrosine Kinases

| Gene Name | Kinase Name | Genbank | Up/Down | # of SD | # of SD | # of SD | Kinase Family | Kinase Group |
|---|---|---|---|---|---|---|---|---|
| PDGFRA | Platelet-derived growth factor receptor, alpha | NM_006206 | Down | 1.5 | 2 | | Tyr | TK |
| SRMS | src-related kinase lacking C-terminal regulatory tyrosine | NM_080823 | Down | 1.25 | 1.75 | | Tyr | TK |

TABLE 1B-continued

Tyrosine Kinases

| Gene Name | Kinase Name | Genbank | Up/Down | # of SD | # of SD | # of SD | Kinase Family | Kinase Group |
|---|---|---|---|---|---|---|---|---|
| | and N-terminal myristylation sites | | | | | | | |
| PTK6 | Protein tyrosine kinase 6 | NM_005975 | Down | 1.25 | 1.5 | | Tyr | TK |
| ZAP70 | zeta-chain (TCR) associated protein kinase 70 kDa | NM_001079 | Down | 1.5 | 2 | | Tyr | TK |
| ERBB4 | v-erb-b2 erythroblastic leukemia viral oncogene homolog 4 (avian) | NM_005235 | Down | 1.25 | 1.5 | | Tyr | TK |
| IGF1R | insulin-like growth factor 1 receptor | NM_000875 | Down | 1 | 1.5 | | Tyr | TK |
| MET | met proto-oncogene (hepatocyte growth factor receptor) | NM_000245 | Down | 1 | 1.5 | | Tyr | TK |
| MERTK | c-mer proto-oncogene tyrosine kinase | NM_006343 | Down | 1 | 1.25 | | Tyr | TK |
| JAK2 | Janus kinase 2 (a protein tyrosine kinase) | NM_004972 | Down | 1 | 1.5 | | Tyr | TK |
| YES1 | v-yes-1 Yamaguchi sarcoma viral oncogene homolog 1 | NM_005433 | Up | 1.25 | 1.25 | | Tyr | TK |
| ERBB3 | v-erb-b2 erythroblastic leukemia viral oncogene homolog 3 (avian) | NM_001982 | Up | 1 | 1 | | Tyr | TK |
| EPHA7 | EphA7 | NM_004440 | Up | 1 | 1.25 | 1.5 | Tyr | TK |
| BTK | Bruton agammaglobulinemia tyrosine kinase | NM_000061 | Up | 1.25 | 1.5 | | Tyr | TK |
| EPHB3 | EphB3 | NM_004443 | Up | 1 | 1.75 | | Tyr | TK |
| RET | ret proto-oncogene (multiple endocrine neoplasia and medullary thyroid carcinoma 1, Hirschsprung disease) | NM_020975 | Up | 3 | | | Tyr | TK |

TABLE 1C

No Protein Phosphorylation Activity

| Gene Name | Kinase Name | Genbank | Up/Down | # of SD | # of SD | # of SD | Kinase Family | Kinase Group |
|---|---|---|---|---|---|---|---|---|
| C8FW | Tribbles homolog 1 | NM_025195 | Down | 1 | 1 | | X | CAMK |
| CHK | Choline kinase | NM_001277 | Down | 1 | 1.5 | | X | GO |
| FLJ13052 | NAD kinase | NM_023018 | Down | 1.25 | 1.75 | | X | GO |
| FLJ22055 | Phosphatidylinositol-4-phosphate 5-kinase, type II, gamma | NM_024779 | Down | 1 | 1 | | X | GO |
| CKMT2 | Creatine kinase, mitochondrial 2 (sarcomeric) | NM_001825 | Down | 1.75 | 2 | | X | GO |
| DKFZP586B1621 | DKFZP586B1621 protein, function unknown | NM_015533 | Down | 1 | 1.25 | | X | GO |
| GK | Glycerol kinase | NM_000167 | Down | 1.5 | 1.75 | | X | GO |
| ITPKC | Inositol 1,4,5-trisphosphate 3-kinase C | NM_025194 | Down | 1 | 1.25 | | X | GO |
| NME4 | Non-metastatic cells 4, protein expressed in | NM_005009 | Down | 1 | 1.25 | | X | GO |
| NM23-H6 | Non-metastatic cells 6, protein expressed in (nucleoside-diphosphate kinase) | NM_005793 | Down | 1.25 | 1.25 | 1.75 | X | GO |
| RBSK | Ribokinase | NM_022128 | Down | 2.25 | | | X | GO |
| ITPKC | Inositol 1,4,5-trisphosphate 3-kinase C | NM_025194 | Down | 1 | 1.25 | | X | GO |
| PMVK | Phosphomevalonate kinase | NM_006556 | Both | 1 | 1.25 | 2.5 | X | GO |
| GS3955 | Tribbles homolog 2 | NM_021643 | Up | 1.25 | 1.25 | | X | CAMK |
| DGKI | diacylglycerol kinase, iota | NM_004717 | Up | 3 | | | X | GO |
| HK2 | hexokinase 2 | NM_000189 | Up | 2.25 | | | X | GO |
| DGKG | diacylglycerol kinase, gamma 90 kDa | NM_001346 | Up | 2.25 | | | X | GO |
| NBP | Coenzyme A synthase (COASY), | NM_025233 | Up | 2.75 | | | X | GO |

TABLE 1C-continued

No Protein Phosphorylation Activity

| Gene Name | Kinase Name | Genbank | Up/Down | # of SD | # of SD | # of SD | Kinase Family | Kinase Group |
|---|---|---|---|---|---|---|---|---|
| DGKA | Diacylglycerol kinase, alpha 80 kDa | NM_001345 | Up | 1.5 | 1.75 | | X | GO |
| XYLB | Xylulokinase homolog (*H. influenzae*) | NM_005108 | Up | 1.25 | 3.5 | | X | GO |
| SPHK2 | Sphingosine kinase 2 | NM_020126 | Up | 1.5 | 2 | | X | GO |
| PRKRA | Protein kinase, interferon-inducible double stranded RNA dependent activator | NM_003690 | Up | 1 | 1 | 2.5 | X | GO |
| PIP5K2A | Phosphatidylinositol-4-phosphate 5-kinase, type II, alpha | NM_005028 | Up | 1 | 1 | | X | GO |

TABLE 2

Kinase whose inhibition modulates synuclein levels

| Gene Name | Kinase Name | Genbank | TF Plates | Up/Down | # of SD | # of SD | # of SD | Kinase Family | Kinase Group |
|---|---|---|---|---|---|---|---|---|---|
| PRKCD | protein kinase C, delta | NM_006254 | 1, 4, 7 | Down | 1 | 1.5 | | Ser/Thr | AGC |
| GPRK2L | G protein-coupled receptor kinase 2-like (*Drosophila*) | NM_005307 | 3, 6, 9 | Down | 1.25 | 1.5 | | Ser/Thr | AGC |
| GPRK5 | G protein-coupled receptor kinase 5 | NM_005308 | 3, 6, 9 | Down | 1.5 | 1.5 | 1.75 | Ser/Thr | AGC |
| AD034 | RIO kinase 1 (yeast) | NM_031480 | 10, 13, 16 | Down | 1.25 | 1.5 | | Ser/Thr | Atypical |
| BRDT | bromodomain, testis-specific | NM_001726 | 12, 15, 18 | Down | 1 | 1.25 | | Ser/Thr | Atypical |
| EEF2K | eukaryotic elongation factor-2 kinase | NM_013302 | 12, 15, 18 | Down | 1.5 | 2.25 | | Ser/Thr | Atypical |
| FASTK | Fas-activated serine/threonine kinase | NM_006712 | 12, 15, 18 | Down | 1.25 | 1.5 | | Ser/Thr | Atypical |
| LOC283629 | Testis-specific serine kinase 4 (TSSK4) | NM_174944 | 21, 24, 27 | Down | 1 | 1 | | Ser/Thr/Tyr | CAMK |
| STK22D | serine/threonine kinase 22D (spermiogenesis associated); TSSK1 | NM_032028 | 21, 24, 27 | Down | 1.25 | 1.25 | | Ser/Thr | CAMK |
| ALS2CR7 | amyotrophic lateral sclerosis 2 (juvenile) chromosome region, candidate 7 | NM_139158 | 28, 31, 34 | Down | 1 | 1.5 | | Ser/Thr | CMGC |
| CLK4 | CDC-like kinase 4 | NM_020666 | 30, 33, 36 | Down | 1 | 1.5 | | Ser/Thr/Tyr | CMGC |
| CDK5 | cyclin-dependent kinase 5 | NM_004935 | 30, 33, 36 | Down | 1 | 2 | | Ser/Thr | CMGC |
| CSNK2A2 | casein kinase 2, alpha prime polypeptide | NM_001896 | 55, 58, 61 | Down | 1 | 1.25 | 1.5 | Ser/Thr | Other |
| MAP2K4 | mitogen-activated protein kinase kinase 4 | NM_003010 | 65, 68, 71 | Down | 1 | 2 | | Ser/Thr/Tyr | STE |
| MAP2K1 | mitogen-activated protein kinase kinase 1 | NM_002755 | 65, 68, 71 | Down | 1 | 1.75 | | Ser/Thr/Tyr | STE |
| MAP2K5 | mitogen-activated protein kinase kinase 5 | NM_002757 | 66, 69, 72 | Down | 1 | 1.25 | | Ser/Thr/Tyr | STE |
| ANKRD3 | ankyrin repeat domain 3 (RIPK4) | NM_020639 | 83, 86, 89 | Down | 1.25 | 1.75 | | Ser/Thr | TKL |
| IRAK3 | interleukin-1 receptor-associated kinase 3 | NM_007199 | 83, 86, 89 | Down | 1 | 1.25 | | Ser/Thr | TKL |

TABLE 2-continued

Kinase whose inhibition modulates synuclein levels

| | | | | | | | | | |
|---|---|---|---|---|---|---|---|---|---|
| BMPR2 | bone morphogenetic protein receptor, type II (serine/threonine kinase) | NM_001204 | 84, 87, 90 | Down | 1 | 2 | | Ser/Thr | TKL |
| PRKG2 | protein kinase, cGMP-dependent, type II | NM_006259 | 1, 4, 7 | Down | 2 | | | Ser/Thr | AGC |
| CHEK2 | CHK2 checkpoint homolog (*S. pombe*) | NM_007194 | 19, 22, 25 | Down | 3.25 | | | Ser/Thr/Tyr | AGC |
| CDK9 | cyclin-dependent kinase 9 (CDC2-related kinase) | NM_001261 | 28, 31, 34 | Down | 2 | | | Ser/Thr | CMGC |
| CDK2 | cyclin-dependent kinase 2 | NM_001798 | 29, 32, 35 | Down | 2 | | | Ser/Thr | CMGC |
| CDKL3 | cyclin-dependent kinase-like 3 | NM_016508 | 29, 32, 35 | Down | 2.25 | | | Ser/Thr | CMGC |
| CDK10 | cyclin-dependent kinase (CDC2-like) 10 | NM_003674 | 29, 32, 35 | Down | 3 | | | Ser/Thr/Tyr | CMCG |
| CDK7 | cyclin-dependent kinase 7 (MO15 homolog, *Xenopus laevis*, cdk-activating kinase) | NM_001799 | 30, 33, 36 | Down | 2 | | | Ser/Thr | CMGC |
| PK428 | CDC42 binding protein kinase alpha (DMPK-like) | NM_003607 | 40, 46, 52 | Down | 2 | | | Ser/Thr/Tyr | GO |
| FLJ32685 | hypothetical protein FLJ32685 | NM_152534 | 57, 60, 63 | Down | 2.75 | | | Ser/Thr/Tyr | Other |
| NEK11 | NIMA (never in mitosis gene a)-related kinase 11 | NM_024800 | 57, 60, 63 | Down | 3.5 | | | Ser/Thr/Tyr | Other |
| JIK | TAO Kinase 3 (MAP3K18) | NM_016281 | 64, 67, 70 | Down | 2 | | | Ser/Thr | STE |
| PAK6 | p21(CDKN1A)-activated kinase 6 | NM_020168 | 65, 68, 71 | Down | 2.25 | | | Ser/Thr | STE |
| KSR | kinase suppressor of ras | NM_013571 | 83, 86, 89 | Down | 2.25 | | | Ser/Thr/Tyr | TKL |
| AMHR2 | anti-Mullerian hormone receptor, type II | NM_020547 | 83, 86, 89 | Down | 2 | | | Ser/Thr/Tyr | TKL |
| LIMK2 | LIM domain kinase 2 | NM_005569 | 84, 87, 90 | Down | 2 | | | Ser/Thr/Tyr | TKL |
| BCR | breakpoint cluster region | NM_004327 | 11, 14, 17 | Both | 1 | 1.25 | 1.5 | Ser/Thr | Atypical |
| ROCK2 | Rho-associated, coiled-coil containing protein kinase 2 | NM_004850 | 2, 5, 8 | Up | 1 | 1 | | Ser/Thr/Tyr | AGC |
| SGK2 | serum/glucocorticoid regulated kinase 2 | NM_170693 | 2, 5, 8 | Up | 1.25 | 1.5 | | Ser/Thr | AGC |
| SGKL | Serum/glucocorticoid regulated kinase-like | NM_013257 | 2, 5, 8 | Up | 1.25 | 1.25 | | Ser/Thr/Tyr | AGC |
| pknbeta | protein kinase N3 | NM_013355 | 3, 6, 9 | Up | 1 | 1.75 | | Ser/Thr | AGC |
| PRKCH | protein kinase C, eta | NM_006255 | 3, 6, 9 | Up | 1 | 1.75 | | Ser/Thr | AGC |
| ROS1 | v-ros UR2 sarcoma virus oncogene homolog 1 (avian) | NM_002944 | 10, 13, 16 | Up | 1 | 1.5 | | Ser/Thr/Tyr | TK |
| CAMK1 | calcium/calmodulin-dependent protein kinase 1 | NM_003656 | 20, 23, 26 | Up | 1.25 | 2 | | Ser/Thr | CAMK |
| CAMK2B | calcium/calmodulin-dependent protein kinase (CaM kinase) II beta | NM_172078 | 20, 23, 26 | Up | 1.5 | 1.75 | | Ser/Thr/Tyr | CAMK |
| CAMK2D | calcium/calmodulin-dependent protein kinase (CaM kinase) II beta | NM_001221 | 21, 24, 27 | Up | 1.5 | 2.25 | | Ser/Thr | CAMK |

TABLE 2-continued

Kinase whose inhibition modulates synuclein levels

| | | | | | | | | | |
|---|---|---|---|---|---|---|---|---|---|
| STK22B | serine/threonine kinase 22B (spermiogenesis associated) | NM_053006 | 21, 24, 27 | Up | 1.25 | 1.25 | | Ser/Thr/Tyr | CAMK |
| STK29 | serine/threonine kinase 29 | NM_003957 | 21, 24, 27 | Up | 1 | 2 | | Ser/Thr/Tyr | CAMK |
| DYRK1B | dual-specificity tyrosine-(Y)-phosphorylation regulated kinase 1B | NM_004714 | 28, 31, 34 | Up | 1 | 1.25 | | Ser/Thr/Tyr | CMGC |
| PCTK1 | PCTAIRE protein kinase 1 | NM_033018 | 28, 31, 34 | Up | 1 | 1.25 | | Ser/Thr | CMGC |
| SRPK2 | SFRS protein kinase 2 | NM_182692 | 30, 33, 36 | Up | 1 | 1.25 | | Ser/Thr/Tyr | CMGC |
| NEK7 | NIMA (never in mitosis gene a)-related kinase 7 | NM_133494 | 55, 58, 61 | Up | 1 | 1 | | Ser/Thr/Tyr | Other |
| PACE-1 | SCY1-like 3 (S. cerevisiae) | NM_020423 | 56, 59, 62 | Up | 1 | 1.5 | | Ser/Thr | Other |
| CNK | cytokine-inducible kinase (polo-like kinase 3 - Drosophila) | NM_004073 | 57, 60, 63 | Up | 1.25 | 2 | | Ser/Thr | Other |
| TTBK | tau tubulin kinase 2 | NM_173500 | 84, 87, 90 | Up | 1.25 | 1.25 | | Ser/Thr/Tyr | CK1 |
| PRKCZ | protein kinase C, zeta | NM_002744 | 3, 6, 9 | Up | 2 | | | Ser/Thr | AGC |
| TTK | TTK protein kinase | NM_003318 | 64, 67, 70 | Up | 2.25 | | | Ser/Thr/Tyr | Other |
| ZAP70 | zeta-chain (TCR) associated protein kinase 70kDa | NM_001079 | 66, 69, 72 | Down | 1.25 | 2 | | Tyr | TK |
| FLT3 | fms-related tyrosine kinase 3 | NM_004119 | 73, 76, 79 | Down | 1 | 1 | | Tyr | TK |
| HCK | hemopoietic cell kinase | NM_002110 | 74, 77, 80 | Down | 1.5 | 1.75 | | Tyr | TK |
| BMX | BMX non-receptor tyrosine kinase | NM_001721 | 74, 77, 80 | Down | 1.25 | 1.5 | | Tyr | TK |
| BTK | Bruton agammaglobulinemia tyrosine kinase | NM_000061 | 74, 77, 80 | Down | 1 | 1 | | Tyr | TK |
| DDR2 | discoidin domain receptor family, member 2 | NM_006182 | 75, 78, 81 | Down | 1 | 1.25 | | Tyr | TK |
| CSF1R | colony stimulating factor 1 receptor, formerly McDonough feline sarcoma viral (v-fms) oncogene homolog | NM_005211 | 75, 78, 81 | Down | 2 | | | Tyr | TK |
| LCK | lymphocyte-specific protein tyrosine kinase | NM_005356 | 39, 45, 51 | Both | 1 | 1.25 | 1.5 | Tyr | GO |
| PRKCA | protein kinase C, alpha | NM_002737 | 1, 4, 7 | Up | 1 | 1.25 | | Tyr | AGC |
| ROR2 | receptor tyrosine kinase-like orphan receptor 2 | NM_004650 | 10, 13, 16 | Up | 1 | 1 | 1 | Tyr | TK |
| PDGFRA | platelet-derived growth factor receptor, alpha polypeptide | NM_006206 | 11, 14, 17 | Up | 1 | 1.25 | | Tyr | TK |
| SRMS | src-related kinase lacking C-terminal regulatory tyrosine and N-terminal myristylation sites | NM_080823 | 11, 14, 17 | Up | 1.25 | 1.25 | | Tyr | TK |

TABLE 2-continued

Kinase whose inhibition modulates synuclein levels

| | | | | | | | | | |
|---|---|---|---|---|---|---|---|---|---|
| TXK | TXK tyrosine kinase | NM_003328 | 12, 15, 18 | Up | 1 | 1.5 | | Tyr | TK |
| YES1 | v-ros UR2 sarcoma virus oncogene homolog 1 (avian) | NM_005433 | 66, 69, 72 | Up | 1.25 | 1.25 | | Tyr | TK |
| DKFZp61P1010 | serine/threonine/tyrosine kinase 1 (STYK1) | NM_018243 | 73, 76, 79 | Up | 1.25 | 1.25 | | Tyr | TK |
| EPHA2 | EphA3 | NM_004431 | 73, 76, 79 | Up | 1 | 1.5 | | Tyr | TK |
| FGR | Gardner-Rasheed feline sarcoma viral (v-fgr) oncogene homolog | NM_005248 | 75, 78, 81 | Up | 1 | 1.25 | | Tyr | TK |
| FLT1 | fms-related tyrosine kinase 1 (vascular endothelial growth factor/vascular permeability factor receptor) | NM_002019 | 75, 78, 81 | Up | 1.25 | 1.5 | | Tyr | TK |
| EPHB3 | EphB3 | NM_004443 | 75, 78, 81 | Up | 1 | 1.25 | | Tyr | TK |
| CSS3R | colony stimulating factor 1 receptor, formerly McDonough feline sarcoma viral (v-fms) oncogene homolog | NM_005211 | 38, 44, 50 | Up | 2.75 | | | Tyr | GO |
| GUCY2C | guanylate cyclase 2C (heat stable enterotoxin receptor) | NM_004963 | 57, 60, 63 | Up | 2.25 | | | Tyr | Other |
| BCKDK | branched chain ketoacid dehydrogenase kinase | NM_005881 | 10, 13, 16 | Down | 1.25 | 1.5 | 2.25 | ? | Atypical |
| BRD4 | bromodomain containing 4 | NM_014299 | 11, 14, 17 | Down | 1.75 | 2 | | ? | Atypical |
| AK3 | adenylate kinase 3 | NM_013410 | 37, 43, 49 | Down | 1 | 1.25 | | X | GO |
| FLJ12476 | hypothetical protein FLJ12476 | NM_022784 | 39, 45, 51 | Down | 1 | 1.25 | | ? | GO |
| PAPSS2 | 3-phosphoadenosine 5-phosphosulfate synthase 2 | NM_004670 | 42, 48, 54 | Down | 1 | 1.5 | | ? | GO |
| C20orf97 | chromosome 20 open reading frame 97 (Tribbles homolog 3) | NM_021158 | 19, 22, 25 | Down | 2 | | | X | CAMK |
| C8FW | Tribbles homolog 1 | NM_025195 | 19, 22, 25 | Down | 2 | | | X | CAMK |
| GS3955 | Tribbles homolog 2 | NM_021643 | 20, 23, 26 | Down | 2 | | | X | CAMK |
| FLJ32704 | chromosome 9 open reading frame 98 | NM_157572 | 37, 43, 49 | Down | 3.75 | | | X | GO |
| DCK | deoxycytidine kinase | NM_000788 | 38, 44, 50 | Down | 2.25 | | | X | GO |
| KIAA0626 | microfibrillar-associated protein 3-like | NM_021647 | 39, 45, 51 | Down | 2.5 | | | X | GO |
| XYLB | Xylulokinase homolog (*H. influenzae*) | NM_005108 | 40, 46, 52 | Down | 3 | | | X | GO |
| UCK1 | uridine-cytidine kinase 1 | NM_031432 | 42, 48, 54 | Down | 2 | | | X | GO |
| GUK1 | guanylate kinase 1 | NM_000858 | 39, 43, 51 | Both | 1 | 2 | 2.75 | ? | GO |
| MGC26954 | chromosome 6 open reading frame 199 | NM_145025 | 40, 46, 52 | Both | 1 | 1 | 1.25 | ? | GO |
| HK1 | hexokinase 1 | NM_033498 | 37, 43, 49 | Up | 2.25 | 2.75 | | X | GO |

TABLE 2-continued

Kinase whose inhibition modulates synuclein levels

| | | | | | | | | | |
|---|---|---|---|---|---|---|---|---|---|
| CALM3 | calmodulin 3 (phosphorylase kinase, delta) | NM_005184 | 38, 44, 50 | Up | 2 | 2.25 | | X | GO |
| RBSK | ribokinase | NM_022128 | 40, 46, 52 | Up | 1.25 | 1.5 | | X | GO |
| PANK1 | pantothenate kinase 1 | NM_148978 | 41, 47, 53 | Up | 1.5 | 1.5 | | X | GO |
| P15RS | hypothetical protein FLJ10656 | NM_018170 | 41, 47, 53 | Up | 1 | 1.5 | | ? | GO |
| PFKFB2 | 6-phosphofructo-2-kinase/fructose-2,6-biphosphatase 2 | NM_006212 | 42, 48, 54 | Up | 1 | 1.25 | | ? | GO |
| CKMT2 | Creatine kinase, mitochondrial 2 (sarcomeric) | NM_001825 | 38, 44, 50 | Up | 3.5 | | | X | GO |
| PGK1 | phosphoglycerate kinase 1 | NM_000291 | 40, 46, 52 | Up | 2.5 | | | X | GO |

Example 2

Verification of Alpha-Synuclein Phosphorylation Modulation by Re-Screening and by qRT-PCR The kinases that showed either an increase or decrease in alpha-synuclein phosphorylation from Example 1 were retested to verify the effect on alpha-synuclein. The confirmation screen was performed using 10 nM siRNA on the targets identified in Example 1 along with several additional kinases of interest. The higher concentration of siRNA in Example 1 was used to ensure that marginal knockdown caused by poorly designed siRNAs could be observed. By using a much lower siRNA concentration in the confirmation screens, the list of candidates could be narrowed down to only those that showed very specific modulation. Some siRNAs that were later reported by Ambion to be ineffective were also re-screened (see Replacement library screen below). Finally, some newly identified kinases were screened and those results were added to the pool of results. The kinases that were identified as candidates were tested by quantitative RT-PCR (qRT-PCR) to confirm that they were actually present in the PEAK-Syn cells (see Example 6). The experimental procedures and results for the confirmation and rescreening were as follows:

Confirmation Screen

The results for the confirmation screen were grouped into four categories shown below:

Completely Confirmed: This category included the kinases for which all three siRNAs produced identical phenotypes in the 10 nM screen and in the 100 nM screen Mostly Confirmed: This category included the kinases for which ⅔ of the siRNAs produced identical phenotypes in the 10 nM and in the 100 nM screen, but one third did not; or, alternatively one siRNA result was replicated, but for a second siRNA there was a trend for the same phenotype but with a different siRNA from that used in the original screen Partly Confirmed: This category included the kinases for which ⅓ of the siRNAs produced the same phenotype in the 10 nM screen and in the 100 nM screen Not Confirmed: This category included the kinases for which either or both of the following occurred:
a) None of the three siRNAs had any effect on phospho alpha-synuclein levels at 10 nM, and/or
b) The siRNAs produced the opposite phenotype to what was observed in the primary 100 nM screen The number of kinases that fell into each category was tabulated and the results are shown in Table 4. Seven kinases were completely confirmed, and they are listed in Table 5. Of these seven, only three were identified as possessing the qualities to be good candidates for a kinase that directly phosphorylates alpha-synuclein at ser-129. This is because only three were both ser/thr kinases and decreased phospho alpha-synuclein levels when the kinase levels were reduced by the specific siRNA. These included: APEG1, which is believed to play a role in growth and differentiation of smooth muscle, PLK2 (SNK), which is expressed in brain and is believed to play a role in normal cell division, and CDC7L1, a cell division cycle protein with kinase activity. Of the three, PLK2 was of the most interest due to its role and localization in cells, specifically activated neurons. α-synuclein is a synaptic-associated protein thought to be involved in synaptic plasticity and vesicular transport. Thus, PLK2 was identified as a very good candidate for a kinase that directly phosphorylates α-synuclein.

TABLE 4

Breakdown of Candidate Hits From 10 nM Confirmation Screen

| Hit Category | Number of Hits |
|---|---|
| Completely Confirmed | 7 |
| Mostly Confirmed | 29 |
| Partly Confirmed | 22 |
| No Reactivity at 10 nM | 19 |
| Opposite Reaction to Primary Screen | 23 |
| Total Number Of Hits Re-Screened at 10 nM | 100 |

NOTES: For all subsequent tables
***denotes where a replacement siRNA has been analyzed and the new data substituted for that from the effective siNRA Key to shading:

| |
|---|
| Significant decrease in phospho-synuclein compared to controls |
| Significant increase in phospho-synuclein compared to controls |

TABLE 5

Completely Confirmed Hits

| Gene Name | Kinase Name | Number of SD siRNA A | Number of SD siRNA B | Number of SD siRNA C | Kinase Family | Kinase Group |
|---|---|---|---|---|---|---|
| APEG1 | Aortic preferentially expressed gene 1 | 1.5 | 1.25 | 1 | Ser/Thr/Tyr | CAMK |
| PLK2/SNK | Polo like kinase 2 | 1.5 | 1.75 | 3.25 | Ser/Thr | Other |
| CDC7L1 | CDC7 cell division cycle 7-like 1 | 2.5 | 1.5 | 1.75 | Ser/Thr | Other |
| PRKG1 | Protein kinase, cGMP-dependent, regulatory, Type I | 1.5 | | 1.75 | Ser/Thr | AGC |
| MAPK13 | Mitogen-activated protein kinase 13 | 2.75 | 6.7 | 4.5 | Ser/Thr/Tyr | CMGC |
| GAK | Cyclin G associated kinase | 2.25 | | | Ser/Thr | Other |
| MET | met proto-oncogene (hepatocyte growth factor receptor) | 2.5 | 1.25 | | Tyr | TK |

Table 5 shows the seven candidates whose results were completely replicated at 10 nM. Only the first three were identified as having strong potential to be a direct kinase, because they are ser/thr kinases that reduce phospho-synuclein levels when the kinase level is reduced.

There were 29 kinases that fell into the mostly confirmed category, 12 of which were candidates for a direct kinase. These are listed in Table 6. There were 17 additional kinases that were mostly confirmed at 10 nM. Although not likely to be a direct kinase, these could play a role in the regulation of a direct kinase and are listed in Table 7. Twenty-two kinases fell into the partly confirmed category. The ser/thr kinases that decreased phospho alpha-synuclein (i.e. potentially a direct kinase for alpha-synuclein) are listed in Table 8, and the remaining potentially regulatory kinases are listed in Table 9.

The ser/thr kinases shown in Table 6 were identified as having potential to be a direct kinase that phosphorylates alpha-synuclein because they significantly reduced phospho-synuclein levels when the kinase level was reduced. ⅔ of the siRNAs produced identical results at 10 nM as they did at 100 nM, and as such, were designated as Mostly Confirmed hits.

The kinases in Table 7 were designated as Mostly Confirmed, because ⅔ of the siRNAs produced identical results at 10 nM and 100 nM concentration of siRNA. However, because they did not produce the appropriate phenotype or were the wrong class of kinase (i.e. tyr or non-protein kinase as opposed to a ser/thr kinase), they were identified as not likely to be a direct kinase that phosphorylates ser-129 on alpha-synuclein. Instead, they may be upstream modulators of alpha-synuclein phosphorylation.

TABLE 6

Potential Direct Serine/Threonine Kinases that Mostly Confirmed at 10 nM siRNA

| Gene Name | Kinase Name | Number of SD siRNA A | Number of SD siRNA B | Number of SD siRNA C | Kinase Family | Kinase Group |
|---|---|---|---|---|---|---|
| FLJ11159 | RIO kinase 2 (yeast) | 2 | *** | *** | Ser/Thr | Atypical |
| ARK5 | AMP-activated protein kinase family member 5 | | 1.25 | 1 | Ser/Thr | CAMK |
| CAMK1 | Calcium/calmodulin-dependent protein kinase I | | 1.25 | 1.75 | Ser/Thr | CAMK |
| CDC2L5 | Cell division cycle 2-like 5 | 2.25 | | | Ser/Thr/Tyr | CMGC |
| ERK8 | Extracellular signal-regulated kinase 8 | 2.25 | 1.25 | 1 | Ser/Thr | CMGC |
| CKIIA2 | Casein kinase 2, alpha prime subunit | 2 | 1 | 2.5 | Ser/Thr | Other |
| MAP2K4 | mitogen-activated protein kinase kinase 4 (MEK4; MKK4; JNKK) | | 2.75 | 1 | Ser/Thr/Tyr | STE |
| MAP2K5 | mitogen-activated protein kinase kinase 5 (MEK5; MKK5) | 1.25 | 2*** | | Ser/Thr/Tyr | STE |
| RIPK3 | receptor-interacting serine-threonine kinase 3 | 2.25 | | | Ser/Thr/Tyr | TKL |
| PRKG2 | protein kinase, cGMP-dependent, type II | 1 | 1.75 | | Ser/Thr | AGC |
| ADRBK1 | adrenergic, beta, receptor kinase 1 (GRK2; BARK1) | | 1.25 | 1.75 | Ser/Thr | AGC |
| RHOK | rhodopsin kinase; G protein-coupled receptor kinase 1; GRK1 | 1.25*** | 2.25*** | | Ser/Thr | AGC |

TABLE 7

Other Kinases That Were Mostly Confirmed at 10 nM siRNA

| Gene Name | Kinase Name | Number of SD siRNA A | Number of SD siRNA B | Number of SD siRNA C | Kinase Family | Kinase Group |
|---|---|---|---|---|---|---|
| CDC42BPB | CDC42 binding protein kinase beta (DMPK-like) | | 3 | | Ser/Thr | AGC |
| PRKCI | protein kinase C, iota | 2 | 1.25 | 1.5*** | Ser/Thr | AGC |
| SMG1 | PI3-kinase-related kinase SMG1 | 3.75 | | 1 | Ser/Thr | Atypical |
| PASK | PAS domain containing serine/threonine kinase | *** | | 1.25 | Ser/Thr | CAMK |
| CDC2 | Cell division cycle 2, G1 to S and G2 to M | | 3 | 1.5 | Ser/Thr/Tyr | CMGC |
| ANKRD3 | ankyrin repeat domain 3 | | 2.25 | | Ser/Thr/Tyr | TKL |
| ADRBK2 | adrenergic, beta, receptor kinase 2 (GRK3; BARK2) | | 6.25 | 1.25 | Ser/Thr | AGC |
| AKT3 | v-akt murine thymoma viral oncogene homolog 3 (protein kinase B, gamma) | 1 | 6.25 | 2*** | Ser/Thr | AGC |
| SDCCAG43 | serologically defined colon cancer antigen 43 | 2.25 | 1 | | Ser/Thr/Tyr | Other |
| ERBB4 | v-erb-b2 erythroblastic leukemia viral oncogene homolog 4 (avian) | 1.75 | 1.75 | | Tyr | TK |
| MERTK | c-mer proto-oncogene tyrosine kinase | | | 1.5 | Tyr | TK |
| ERBB3 | v-erb-b2 erythroblastic leukemia viral oncogene homolog 3 (avian) | | 1.75 | | Tyr | TK |
| CHK | Choline kinase | | 1.75 | | Non-protein | GO |
| CKMT2 | Creatine kinase, mitochondrial 2 (sarcomeric) | | 2.5 | 1.25 | Non-protein | GO |
| NM23-H6 | Non-metastatic cells 6, protein expressed in (nucleoside-diphosphate kinase) | 1.5 | | 1.5 | Non-protein | GO |
| RBSK | Ribokinase | 2 | 1.75 | 2.25 | Non-protein | GO |
| SPHK2 | Sphingosine kinase 2 | 1.5 | 1 | | Non-protein | GO |

TABLE 8

Potential Direct Serine/Threonine Kinases that Partly Confirmed at 10 nM siRNA

| Gene Name | Kinase Name | Number of SD siRNA A | Number of SD siRNA B | Number of SD siRNA C | Kinase Family | Kinase Group |
|---|---|---|---|---|---|---|
| GPRK6 | G protein-coupled receptor kinase 6 | | 1.25 | 1 | Ser/Thr | AGC |
| PDPK1 | 3-Phosphoinositide dependent protein kinase-1 | | 2.75 | 1 | Ser/Thr | AGC |
| PRKAA2 | Protein kinase, AMP-activated, alpha 2 catalytic subunit | 1 | 4.75 | 1 | Ser/Thr | CAMK |
| CDK8 | Cyclin-dependent kinase 8 | 2.25 | | | Ser/Thr | CMGC |
| CKIIA1 | Casein kinase 2, alpha subunit | 3.5 | | | Ser/Thr | Other |
| TESK2 | testis-specific kinase 2 | *** | 1.5 | | Ser/Thr/Tyr | TKL |
| JIK | TAO Kinase 3 (MAP3K18) | 1.25 | 1.25 | 1.5 | Ser/Thr | STE |
| PAK6 | p21(CDKN1A)-activated kinase 6 | | | 1 | Ser/Thr | STE |

The ser/thr kinases in Table 8 were identified as having potential to be a direct kinase that phosphorylates alpha-synuclein because they significantly reduced phospho-synuclein levels when the kinase levels were reduced. Only ⅓ of the siRNAs produced identical results at 10 nM as they did at 100 nM, and as such, were designated as Partly Confirmed hits. Several candidates had contradictory results, and, thus, were identified as having less potential to be a direct kinase for alpha-synuclein.

nuclein phenotype, indicating that the results for these kinases from the 100 nM screen were due to off-target effects. Twenty-three kinases (Table 11) produced the opposite effect on phospho-alpha-synuclein levels at 10 nM than at 100 nM siRNA. There is a possibility that the results at 10 nM were the true effects due to the fact that at 100 nM, results are sometimes masked by off-target effects. This can happen at the much higher siRNA concentration. Alternatively, the true

TABLE 9

Other Kinases That Were Partly Confirmed at 10 nM siRNA

| Gene Name | Kinase Name | siRNA A | siRNA B | siRNA C | Kinase Family | Kinase Group |
|---|---|---|---|---|---|---|
| CDK5 | Cyclin-dependent kinase 5 | 2.25 | | 1 | Ser/Thr | CMGC |
| PRKWNK1 | Protein kinase, lysine deficient 1 | | 1.75 | 1 | Ser/Thr | Other |
| DAPK1 | Death-associated protein kinase 1 | | 3.5 | | Ser/Thr | CAMK |
| STK35 | Serine/threonine kinase 35, Clik 1 | 1.25 | 1.25 | | Ser/Thr | Other |
| PKMYT1 | Protein kinase, membrane-associated, tyrosine/threonine 1 | 5.75 | 1.5 | | Ser/Thr/Tyr | Other |
| IKBKE | inhibitor of kappa light polypeptide gene enhancer in B-cells, kinase epsilon | | 1.5 | | Ser/Thr | Other |
| RET | ret proto-oncogene (multiple endocrine neoplasia and medullary thyroid carcinoma 1, Hirschsprung dis) | 3.75 | 8.25 | 1.75 | Tyr | TK |
| FLJ3052 | NAD kinase | | | 1.25 | Non-protein | GO |
| DKFZP586B1621 | DKFZP586B1621 protein, function unknown | 1.5 | | 1.25 | Non-protein | GO |
| ITPKC | Inositol 1,4,5-trisphosphate 3-kinase C | | 2 | 1.5 | Non-protein | GO |
| PMVK | Phosphomevalonate kinase | 1.75 | | 2 | Non-protein | GO |
| NBP | Coenzyme A synthase (COASY), | 1 | 5.75*** | | Non-protein | GO |
| PRKRA | Protein kinase, interferon-inducible double stranded RNA dependent activator | | 1 | | Non-protein | GO |
| PIP5K2A | Phosphatidylinositol-4-phosphate 5-kinase, type II, alpha | | 1.5 | | Non-protein | GO |

The kinases in Table 9 were identified as having less potential to be direct kinases in the phosphorylation of alpha-synuclein at ser-129 but could be upstream modulators of alpha-synuclein phosphorylation. ⅓ of the siRNAs produced identical results at 10 nM as they did at 100 nM, and as such, were designated as Partly Confirmed hits. However, several had contradictory results and, thus, were designated as having less potential to be direct kinases of alpha-synuclein.

Forty-two kinases did not have their initial results confirmed at 10 nM. Of these, 19 fell into category a) listed above, and are listed in Table 10. At 10 nM, none of the three siRNAs at 10 nM produced any change in the phospho-alpha-syeffect may have been seen at the higher concentration. In any case, these kinases were designated as less likely to be direct kinases of alpha-synuclein.

The nineteen kinases shown in Table 10 had no significant reactivity at 10 nM compared to controls. Thus, it is possible that the change in phospho-synuclein levels observed at 100 nM was due to off-target effects caused by high concentrations of siRNA. GPRK5 and GPRK7 were not candidates in the original 100 nM screen, but were analyzed at 10 nM siRNA because of additional interest in their role in alpha-synuclein phosphorylation.

TABLE 10

Kinases That Had No Reactivity at 10 nM siRNA

| Gene Name | Kinase Name | Number of SD siRNA A | siRNA B | siRNA C | Kinase Family | Kinase Group |
|---|---|---|---|---|---|---|
| CAMK2D | Calcium/calmodulin-dependent protein kinase II-delta | | *** | | Ser/Thr | CAMK |
| CDK4 | Cyclin-dependent kinase 4 | | | | Ser/Thr** | CMGC |
| CLK3 | CDC-like kinase 3 | | | | Ser/Thr/Tyr | CMGC |
| PRP4 | Pre-mRNA processing factor 4 homolog B (yeast) | | | | Ser/Thr | GO |
| JAK2 | Janus kinase 2 (a protein tyrosine kinase) | | | | Tyr | TK |
| CDK10 | cyclin-dependent kinase (CDC2-like) 10 | | | | Ser/Thr/Tyr | CMGC |
| FLJ10074 | SCY1-like 2 (*S. cerevisiae*) | *** | *** | *** | Ser/Thr | Other |
| FLJ32685 | hypothetical protein FLJ32685 | *** | | | Ser/Thr/Tyr | Other |
| NEK11 | NIMA (never in mitosis gene a)-related kinase 11 | | | | Ser/Thr/Tyr | Other |
| GPRK7 | G protein-coupled receptor kinase 7; GRK7 | No siRNA | 2 | 2 | Ser/Thr | AGC |
| GPRK5 | G protein-coupled receptor kinase 5; GRK5 | *** | | 1.25 | Ser/Thr | AGC |
| PDGFRA | Platelet-derived growth factor receptor, alpha | | | | Tyr | TK |
| PTK6 | Protein tyrosine kinase 6 | | | | Tyr | TK |
| IGF1R | insulin-like growth factor 1 receptor | *** | | | Tyr | TK |
| EPHB3 | EphB3 | | | | Tyr | TK |
| YES1 | v-yes-1 Yamaguchi sarcoma viral oncogene homolog 1 | | | | Tyr | TK |
| C8FW | Tribbles homolog 1 | | | | Non-protein | CAMK |
| FLJ22055 | Phosphatidylinositol-4-phosphate-5 kinase, type II, gamma | | | | Non-protein | GO |
| DGKA | Diacylglycerol kinase, alpha 80kDa | | | | Non-protein | GO |

The results for the kinases in Table 11 were not confirmed at 10 nM because they had the opposite effect on phospho-synuclein levels from that seen at 100 nM. However, it is possible that the results at 10 nM siRNA were the true results, and that the high concentration (100 nM) of siRNA was masking the true effects. It is also possible that the initial effects observed at 100 nM were the true effects. These were designated as likely to be direct kinases of alpha-synuclein and set aside to be tested further at a later date.

TABLE 11

Kinases Whose Results Were Opposite To The Primary Screen

| Gene Name | Kinase Name | Number of SD siRNA A | siRNA B | siRNA C | Kinase Family | Kinase Group |
|---|---|---|---|---|---|---|
| SSTK | Serine/threonine protein kinase SSTK | 1.25 | | | Ser/Thr | CAMK |
| PHKG2 | Phosphorylase kinase, gamma 2 (testis) | 1*** | *** | *** | Ser/Thr | CAMK |
| CASK | Calcium/calmodulin-dependent serine protein kinase | 1.75 | | | Ser/Thr | CAMK |
| MAP2K1 | mitogen-activated protein kinase kinase 1 (MEK1; MKK1) | 2 | | 1.5 | Ser/Thr/Tyr | STE |
| BRD3 | Bromodomain-containing protein 3 | | *** | 1*** | Ser/Thr | Atypical |

TABLE 11-continued

Kinases Whose Results Were Opposite To The Primary Screen

| | | | | | | |
|---|---|---|---|---|---|---|
| LOC283629 | Chromosome 14 open reading frame 20; Testis-specific serine kinase 4 | 1.75 | | | Ser/Thr/Tyr | CAMK |
| IRAK3 | Interleukin-1 receptor-associated kinase 3 | 1.25 | 1.75 | | Ser/Thr | TKL |
| LIMK2 | LIM domain kinase 2 | 2.25 | | | Ser/Thr/Tyr | TKL |
| EIF2AK3 | eukaryotic translation initiation factor 2-alpha kinase 3 | 2.5 | 1.75 | | Ser/Thr | Other |
| BIKE | BMP2 inducible kinase (BMP2K), transcript variant | 3.75 | 1 | 1.5 | Ser/Thr/Tyr | Other |
| TTK | TTK protein kinase | | 1.5 | 1.25 | Ser/Thr | Other |
| GPRK2L | G protein-coupled receptor kinase 2 like; GRK4 | | | 1 | Ser/Thr | AGC |
| SRMS | src-related kinase lacking C-terminal regulatory tyrosine and N-terminal myristylation sites | | 2.75 | 3.5 | Tyr | TK |
| ZAP70 | zeta-chain (TCR) associated protein kinase 70kDa | 1.5*** | *** | | Tyr | TK |
| EPHA7 | EphA7 | | | 1.5 | Tyr | TK |
| BTK | Bruton agammaglobulinemia tyrosine kinase | 1.5 | | 1 | Tyr | TK |
| GK | Glycerol kinase | | 1.25 | | Non-protein | GO |
| NME4 | Non-metastatic cells 4, protein expressed in | *** | 4 | | Non-protein | GO |
| GS3955 | Tribbles homolog 2 | | 1 | 1.25 | Non-protein | CAMK |
| DGKI | diacylglycerol kinase, iota | 1.25 | | | Non-protein | GO |
| HK2 | hexokinase 2 | | | 1 | Non-protein | GO |
| DGKG | diacylglycerol kinase, gamma 90kDa | | 1.5 | | Non-protein | GO |
| XYLB | Xylulokinase homolog (*H. influenzae*) | 1 | | | Non-protein | GO |

Replacement and Up-Dated Library Screens

Because some siRNAs used in the initial screen were later identified as being of poor quality, screens were performed at both concentrations with replacement siRNAs. The data for the replacement siRNAs was used to replace the data for that specific siRNA result from the original screen. Statistical data was tabulated for the three siRNAs for each kinase, and using this, nine additional kinases were identified as candidates from the original screen that were missed in the primary screen. These were retested, and two of the kinases were partially confirmed at 10 nM siRNA. These were BCKDK and FLJ25965 (KSR2).

During the process, a number of new kinases were identified and siRNAs became available. These were tested as in Example 1 as an AMBION Up-Dates library and new kinase candidates were identified. Many of the newly identified kinases fell under the GO (Gene Ontology Consortium) classification. As such, it was difficult to find detailed information on some of these kinases. Several of the genes included in this category were not true kinases, but were kinase binding proteins or adaptor proteins. At 10 nM siRNA, thirteen kinases were confirmed to be candidates for directly acting on alpha-synuclein. Two of these were likely candidates for being a direct kinase, see Table 12. The remaining eleven were designated as possible indirect regulators of phospho-synuclein levels, see Table 12. Table 12 provides Genbank accession numbers for the kinase sequences as deposited in Genbank as of Nov. 1, 2005.

TABLE 12

Potential Kinase Hits From the Ambion Updates Library

| Gene Name | Genbank # | Kinase Name | siRNA A | siRNA B | siRNA C | Kinase Family |
|---|---|---|---|---|---|---|
| IKBKB | NM_001556 | inhibitor of kappa light polypeptide gene enhancer in B-cells, kinase beta | 1.75 | 1.25 | | Ser/Thr |
| PRKAG1 | NM_212461 | protein kinase, AMP-activated, gamma 1 non-catalytic subunit | 1 | | 1 | Ser/Thr |
| LOC375449 | NM_198828 | similar to microtubule associated testis specific serine/threonine protein kinase | 2 | | | Ser/Thr |

TABLE 12-continued

Potential Kinase Hits From the Ambion Updates Library

| | | | | | | |
|---|---|---|---|---|---|---|
| PRKRIR | NM_004705 | protein-kinase, interferon-inducible double stranded RNA dependent inhibitor, repressor of (P58 repressor) | 1.25 | | 1.25 | Ser/Thr |
| DLG3 | NM_021120 | discs, large homolog 3 (neuroendocrine-dlg, *Drosophila*) | | 2.5 | 1 | Non-protein |
| DLG4 | NM_001365 | discs, large homolog 4 (*Drosophila*) | 1.25 | 1.25 | | Non-protein |
| PIK3CG | NM_002649 | phosphoinositide-3-kinase, catalytic, gamma polypeptide | | 1 | 1.5 | Non-protein |

| | | | | | | |
|---|---|---|---|---|---|---|
| LIM | NM_006457 | PDZ and LIM domain 5 | | 1 | 1.5 | Not a kinase |
| PCM1 | NM_006197 | pericentriolar material 1 | 1.25 | | 1 | Not a kinase |
| PIK3AP1 | NM_152309 | phosphoinositide-3-kinase adaptor protein 1 | | 2 | | Not a kinase |
| AKAP1 | NM_003488, NM_139275 | A kinase (PRKA) anchor protein 1 | 1 | 1.25 | 1 | Kinase Binding Protein |

| | | | | | | |
|---|---|---|---|---|---|---|
| CIB2 | NM_006383 | calcium and integrin binding family member 2 | | 1.25 | 1 | Regulatory, not a kinase |
| CKIIB | NM_001320 | casein kinase 2, beta polypeptide | 2.25 | 1.25 | 2 | Regulatory subunit |

A summary of the results showing the kinase siRNAs that were identified and verified in Examples 1 and 2 are shown in Tables 13 and 14. From these results, PLK2, APEG1, CDC7L1, MET, IKBKB, CKII, GRK 1, 2, 6 and 7 were identified as kinases that are very likely to phosphorylate alpha-synuclein directly or indirectly. The kinases that were identified as having siRNAs that increased alpha-synuclein phosphorylation (PRKG 1, MAPK13, and GAK) could very well be negative regulators of alpha-synuclein phosphorylation.

Tables 13 and 14: Summary of Confirmation studies

TABLE 13

| | | Original Screen, 100 nM | | | Confirmation Screen, 10 nM | | |
|---|---|---|---|---|---|---|---|
| | | Number of SD above or below SynP mean | | | Number of SD above or below SynP mean | | |
| Gene Name | Kinase Name | siRNA A | siRNA B | siRNA C | siRNA A | siRNA B | siRNA C |
| APEG1 | Aortic preferentially expressed gene 1 | 2.25 | 1.75 | 2 | 1.5 | 1.25 | 1 |
| SNK/PLK2 | Polo like kinase 2 | 2.25 | 1 | 1.5 | 1.5 | 1.75 | 3.25 |
| CDC7L1 | CDC7 cell division cycle 7-like 1 | 1.25 | 2 | 3 | 2.5 | 1.5 | 1.75 |

| | | | | | | | |
|---|---|---|---|---|---|---|---|
| PRKG1 | Protein kinase, cGMP-dependent, regulatory, Type I | 1.25 | | 1 | 1.5 | | 1.75 |
| MAPK13 | Mitogen-activated protein kinase 13 | 1.25 | 1 | 1.75 | 2.75 | 6.7 | 4.5 |
| GAK | Cyclin G associated kinase | 1.75 | | | 2.25 | | |
| MET | met proto-oncogene (hepatocyte growth factor receptor) | 1.5 | 1 | | 2.5 | 1.25 | |

TABLE 14

GRK Results - Mixture of Mostly, Partially and Not Confirmed

| | | Original Screen, 100 nM | | | Confirmation Screen, 10 nM | | |
|---|---|---|---|---|---|---|---|
| | | Number of SD above or below SynP mean | | | Number of SD above or below SynP mean | | |
| Gene Name | Kinase Name | siRNA A | siRNA B | siRNA C | siRNA A | siRNA B | siRNA C |
| RHOK | rhodopsin-kinase; G protein-coupled receptor kinase 1; GRK1 | | 1 | | 1.25*** | 2.25*** | |
| ADRBK1 | adrenergic, beta, receptor kinase 1 (GRK2; BARK1) | | | 1.5 | | 1.25 | 1.75 |
| ADRBK2 | adrenergic, beta, receptor kinase 2 (GRK3; BARK2) | | 2 | | | 6.25 | 1.25 |
| GPRK2L | G protein-coupled receptor kinase 2 like; GRK4 | 1.75 | | | | | 1 |
| GPRK5 | G protein-coupled receptor kinase 5; GRK5 | | | | *** | | 1.25 |
| GPRK6/GRK6 | G protein-coupled receptor kinase 6 | 1.25 | | 1.25 | | 1.25 | 1 |
| GPRK7 | G protein-coupled receptor kinase 7; GRK7 | | | | No siRNA | 2 | 2 |

In the following examples, in vitro kinase assays were performed on a number of the potential targets identified in Examples 1 and 2.

Example 3

Identification of Direct Phosphorylation of Alpha-Synuclein In Vitro

To determine which of the kinase(s) from the siRNA screen directly phosphorylated alpha-synuclein, purified kinases were incubated with alpha-synuclein in in vitro kinase reactions. These results showed that PLK2, GRK2, 5, 6. and 7 (GPRK2, 5, 6 and 7) were all capable of phosphorylating alpha-synuclein specifically at Serine 129 and did not phosphorylate Serine 87 in vitro, showing that they could directly phosphorylate alpha-synuclein. MET, CDC7L1, and IKBKB were shown to be incapable of directly phosphorylating alpha-synuclein (FIGS. 1A-C).

Assay conditions for testing recombinant kinase activities toward recombinant alpha-synuclein at Serine 129 were established and found to be reproducible by immunoblot and ELISA analyses. Commercially available recombinant kinases were used when possible. Those that were not available were produced as indicated by recombinant means.

Figure 1B:
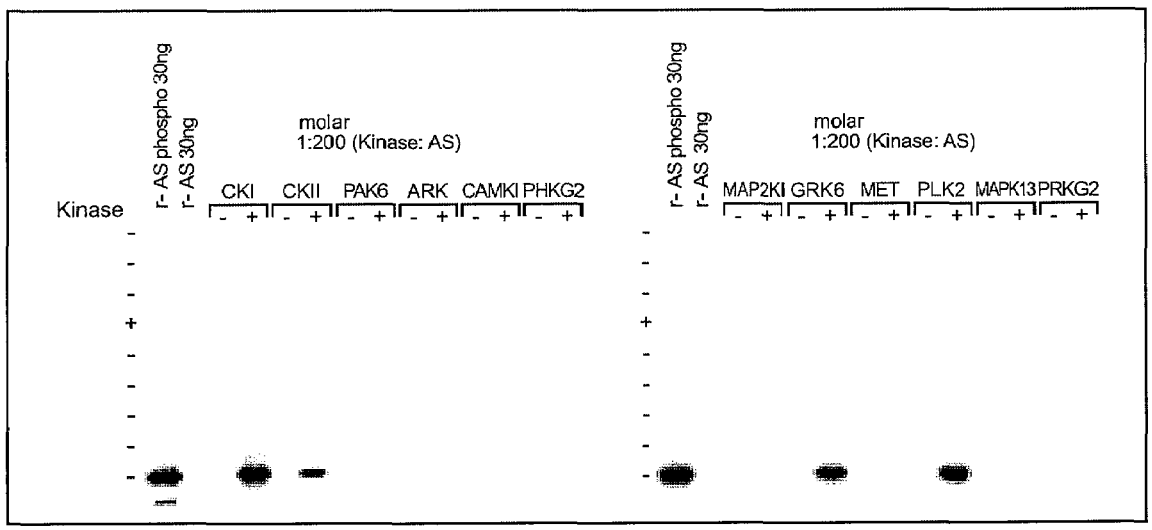
Figure 1C:
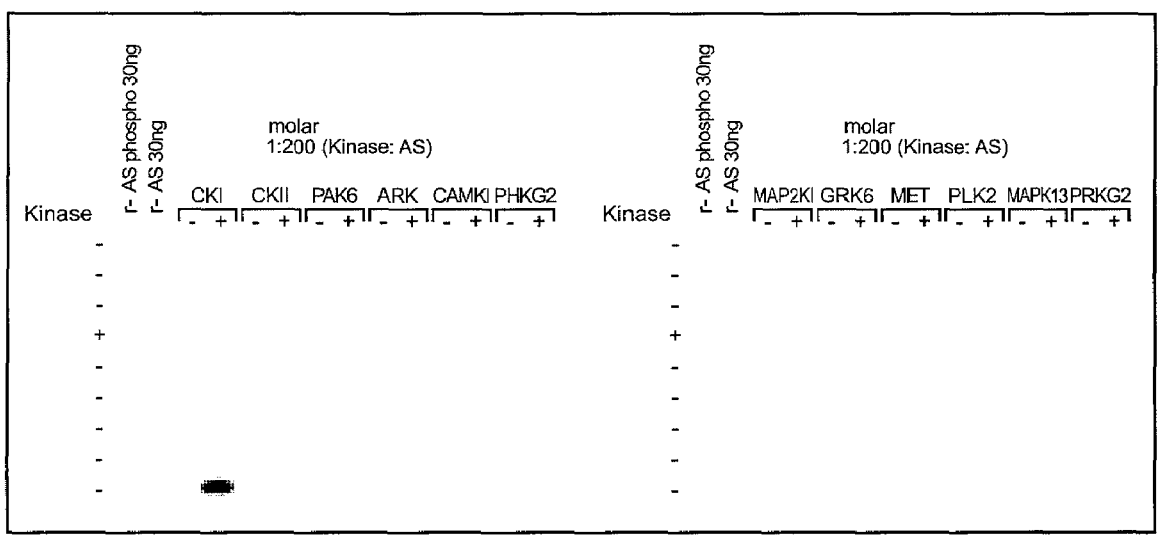

In FIGS. 1A-C, recombinant kinases were included in the in vitro alpha-synuclein (AS) assay by standardizing kinase to alpha-synuclein substrate at a constant molar ratio (derived from MW of predicted mature protein) in each reaction (1:200; kinase: recombinant alpha-synuclein kinase—rAS). − control, + kinase; In FIG. 1A, a probe for total alpha-synuclein (AS) (mAb Syn-1; 0.1 µg/mL) was used indicating equivalent substrate in each reaction; In FIG. 1B, a parallel blot was probed for S129 phosphorylation (mAb 11A5 1 µg/mL). Prominent signals came from GRK6, CKI, CKII and PLK2 (not previously tested by activity normalization). In FIG. 1C, a parallel blot probed for S87 phosphorylation (pAb, ELADW-110 5 µg/mL). A signal was detected only with CKI phosphorylation.

Figure 1D:
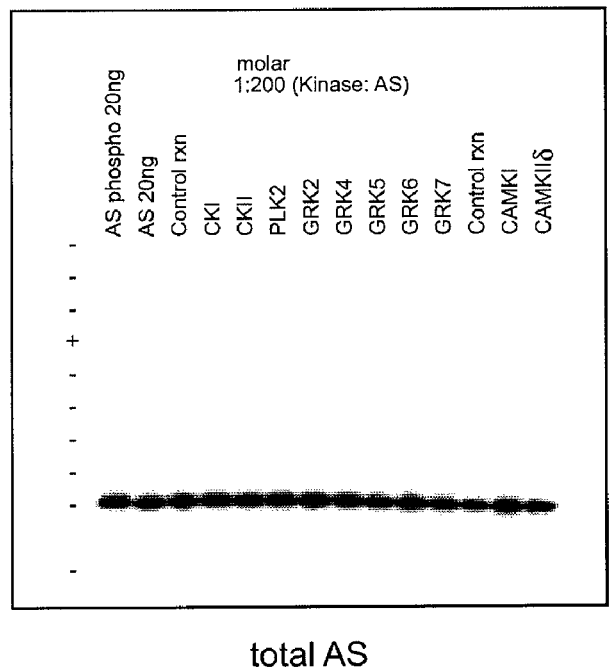
FIGS. 1D-F show a more focused study with recombinant kinases from the GPCR-receptor kinase (GRK) family and PLK2.
Figure 1E:
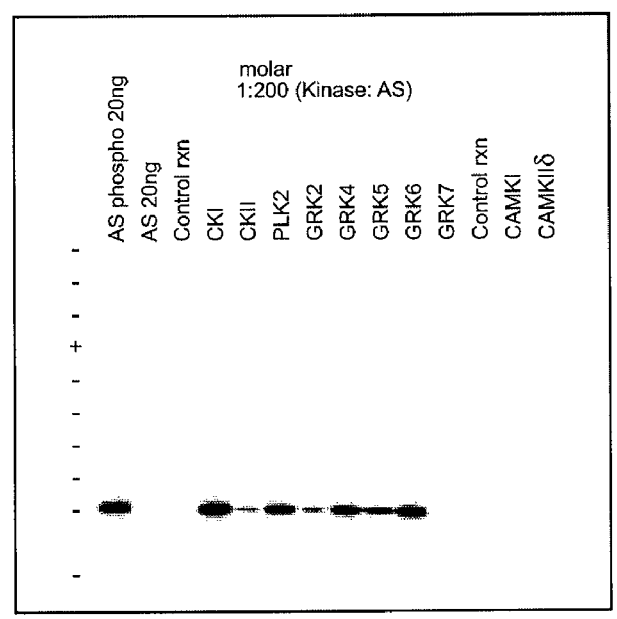
Figure 1F:
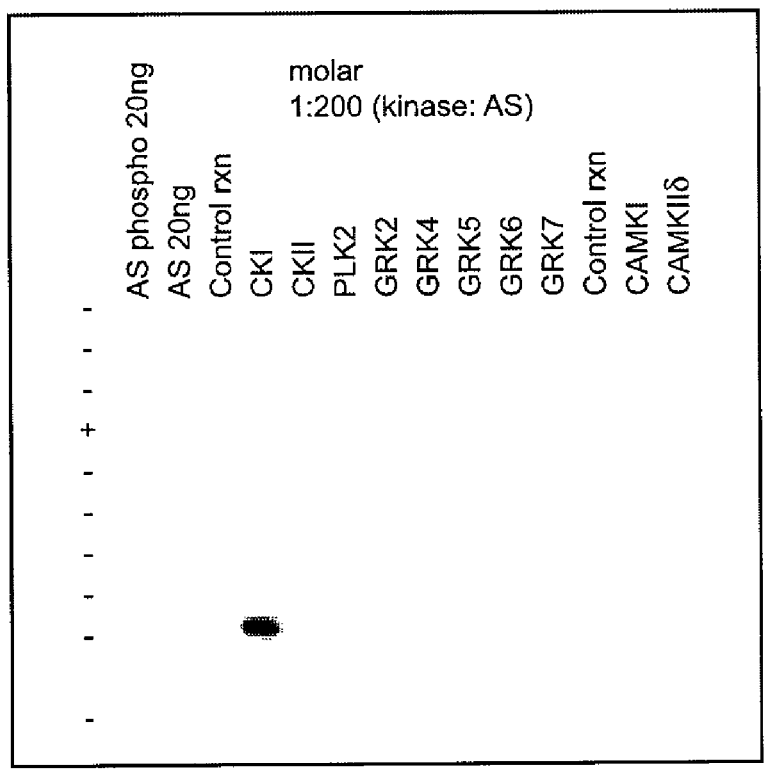

In FIGS. 1D-F, a more focused study was performed with recombinant kinases from the GPCR-receptor kinase (GRK) family and PLK2 were included in the in vitro alpha-synuclein (AS) assay by standardizing kinase to AS substrate at a constant molar ratio (derived from MW of predicted mature protein) in each reaction (1:200; kinase: rAS). − control, + kinase; CAM kinases served as negative controls while CKI and II served as positive controls. In FIG. 1D, a probe for total AS (mAb Syn-1; 0.1 µg/mL) was used indicating equivalent substrate in each reaction; In FIG. 1E, a parallel blot probed for S129 phosphorylation (mAb 11A5 1 µg/mL). Prominent signals came from all GRKs except for GRK7. A specificity between GRK members could be seen with signal and can be represented as: CKI>GRK6>PLK2>GRK4>GRK5>GRK2. In FIG. 1F, a parallel blot probed for S87 phosphorylation (pAb, ELADW-110 5 µg/mL). Signal was detected only with CKI phosphorylation.

The assay conditions are defined in Table 15 and were held constant for all kinases tested. All of the kinases listed were available as tagged/recombinant protein with the exception of CDC7L1, PRKG1 and APEG. Those putative targets were expressed in an in vitro translation system and tested in the in vitro AS assay without protein concentration or activity measurements.

TABLE 15

Assay conditions for in vitro kinase reactions:

| # | Kin | Confirmation | MW kinase | 1:200 kinase:AS (molarity) ng kinase; ul in 100 ul rxn | total ul kin. in stock | ng/ul kin | Units/ul | Dilution | Total ul kin./rxn | ng kin/rxn | co-factors |
|---|---|---|---|---|---|---|---|---|---|---|---|
| 1 | CKI a' | most | 49000 delta | 5.1 ng; 6.3 ul (1000x dilution) | 20 | 814 | 1000 | 100000x (0.01 U/ul) | 3 | 0.024 | |
| 2 | CKII a' | part | 44,000 alpha 26,000 beta | 4.6 ng; 4.3 ul (1000x dilution) | 20 | 1070 | 500 | 50000x (0.01 U/ul) | 3 | 0.0642 | |
| 3 | PAK6 | part | 38,000 | 4 ng; 1 ul (100x dilution) | 50 | 100 | 0.21 | 10x (0.021 U/ul) | 1.43 | 14.3 | |
| 4 | ARK5 | most | 78,000 | 8.1 ng; 8.1 ul (100x dilution) | 50 | 100 | 0.06 | | 0.5 | 50 | |
| 5 | CaMK1 | most | 68,000 | 7.1 ng; 7.1 ul (100x dilution) | 50 | 100 | 0.29 | 10x (0.029 U/ul) | 1 | 10 | calmodulin 1 uM |
| 20 | PDK1 | part | 59,000 | 6.1 ng; 3 ul (200x dilution) | 50 | 200 | 0.074 | 10x (0.0074 U/ul) | 4.05 | 81 | SGK |
| 6 | PHKG2 | del | 52,000 | 5.4 ng; 7.7 ul (100x dilution) | 143 | 70 | 0.007 | | 4.3 | 301 | |
| 7 | MAP2K1 | del | 49,000 | 5.1 ng; 5.1 ul (100x dilution) | 20 | 500 | 1.69 | 100x (0.00169 U/ul) | 17.75 | 90 | |
| 8 | GRK6 | part | 94,000 | 9.8 ng; 3 ul (100x dilution) | 34 | 290 | 0.008 | | 3.75 | 1088 | |
| 9 | CAMKIIdelta | del | 59,000 | 6.2 ng; 1.9 ul (100x dilution) | 31 | 320 | 4.93 | 100x (0.0493 U/ul) | 0.61 | 195 | calmodulin 1 uM |
| 10 | Met | conf | 50,000 | 5.2 ng; 5.2 ul (100x dilution) | 50 | 100 | 0.022 | | 1.363 | 136 | |
| 11 | MAPK13 | conf | 46,000 | 4.8 ng; 1.1 ul (100x dilution) | 22 | 450 | 0.054 | | 0.56 | 250 | |
| 12 | PRKG2 | most | 117,000 | 12.2 ng; 2.8 ul (100x dilution) | 22 | 440 | 0.017 | | 1.76 | 776 | |
| 13 | PLK2 | conf | 106,000 | 11 ng; 4.1 ul (100x dilution) | 27 | 270 | 0.027 | | 1.1 | 297 | |
| 14 | GRK2 | most | 82,300 | 8.6 ng; 1.7 ul (100x dilution) | 20 | 500 | 0.0045 | | 6.7 | 3350 | |
| 15 | GRK4 | part | 94,000 | 9.8 ng; 2.5 ul (100x dilution) | 25 | 400 | 0.0012 | | 25 | 10,000 | |
| 16 | GRK5 | part | 95,200 | 9.9 ng; 2.1 ul (100x dilution) | 21 | 480 | 0.00018 | 167 | 80,160 | | |
| 17 | GRK7 | part | 89,700 | 9.3 ul; 1.9 ul (100x dilution) | 21 | 480 | 0.00067 | | 45 | 21,600 | |
| 18 | CDC7L1 | conf | 63,800 | undetermined; in vitro translation | nd | nd | nd | | nd | nd | |
| 19 | PRKG1 | conf | 76,200 | undetermined; in vitro translation | nd | nd | nd | | nd | nd | |
| 24 | APEG | conf | 12,600 | undetermined; in vitro translation | nd | nd | nd | | nd | nd | |

The Standard Conditions were: 40 mM MOPS-NaOH; 1 mM EDTA MgCl 10 mM pH 8.0, 0.1% BME; 0.01% Brij-35; 5 ug BSA, 100 uM ATP (5× [substrate]), 100 uL volume; 300 ng r-wt-AS (208 nM), (1:200 kinase: AS or activity normalized 0.03 U/rxn, 34C; 17 hrs. Further, those kinases with varying levels of significance/confirmation from combined screening data were purchased as recombinant, tagged protein, annotated and incorporated into a table format for the purposes of establishing in vitro assays that were comparable based upon normalization to activity units (determined by the manufacturer from synthetic substrates) or substrate:enzyme molar ratios determined from MW and reaction volume. The details of reaction conditions are stipulated in Table 15. Kin.=kinase. For Confirmation: Most=mostly, Part=partially, del=deleted, conf=confirmed.

Figure 2A:
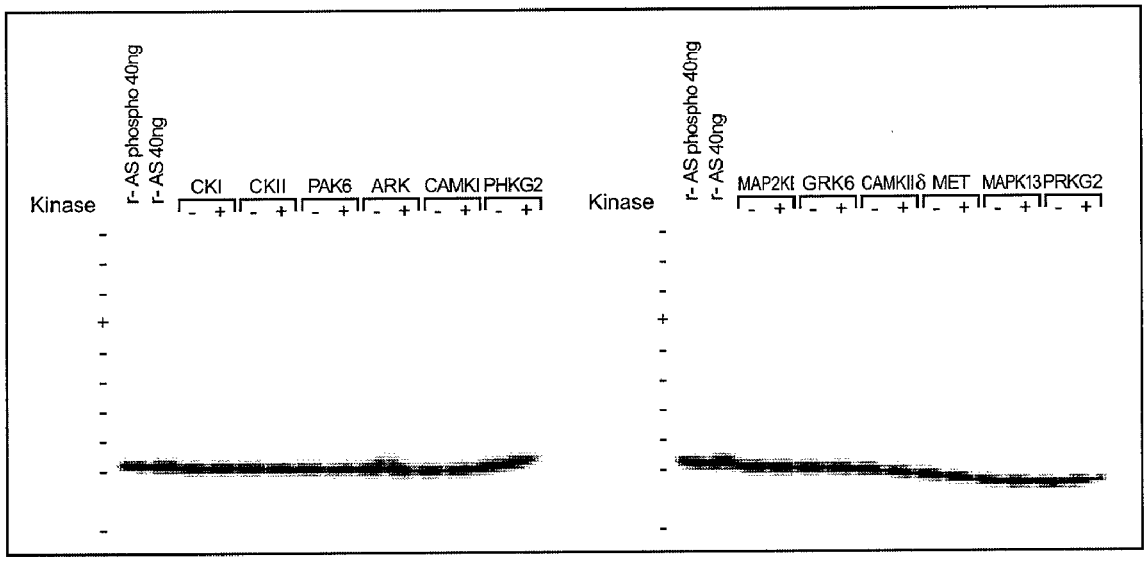
FIGS. 2A and B show the results of kinase activity in vitro for various kinases.
Figure 2B:
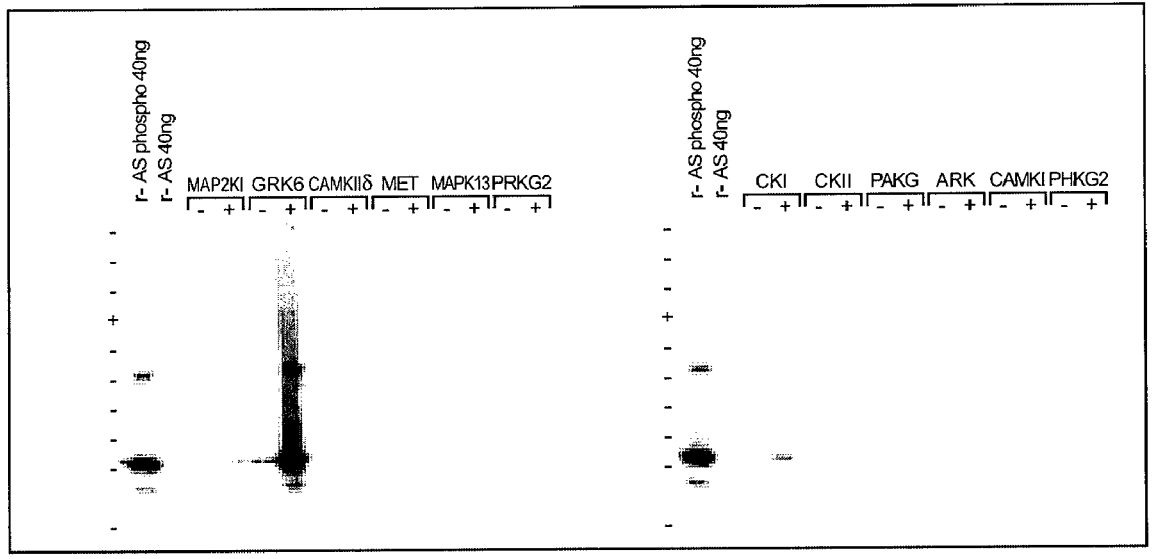
FIG. 2B shows Serine 129.

Kinase activity was initially tested against AS by activity units as determined from non-native substrates (peptides or casein). This method was used to get a rough estimate as to specificity between kinases and whether AS was an in vitro substrate for the kinase panel. The results of this study are found in FIGS. 2 and 3. At the time of this experiment, only a portion of available kinases were obtained and ⅔ kinases from the "most probable 7 confirmed" were included (PLK2 was not tested). The most prominent result came from GRK6 (G-protein coupled receptor kinase 6). CKI gave modest activity and CKII was not detectable. Because both CK kinases are known to phosphorylate S129 AS, normalization by activity units was biased against those kinases which had higher specific activity for tested substrates vs AS. This was likely the situation for GRK6 which might have preferred AS as a substrate rather than the peptide substrate which defined its activity units.

Figure 3A:
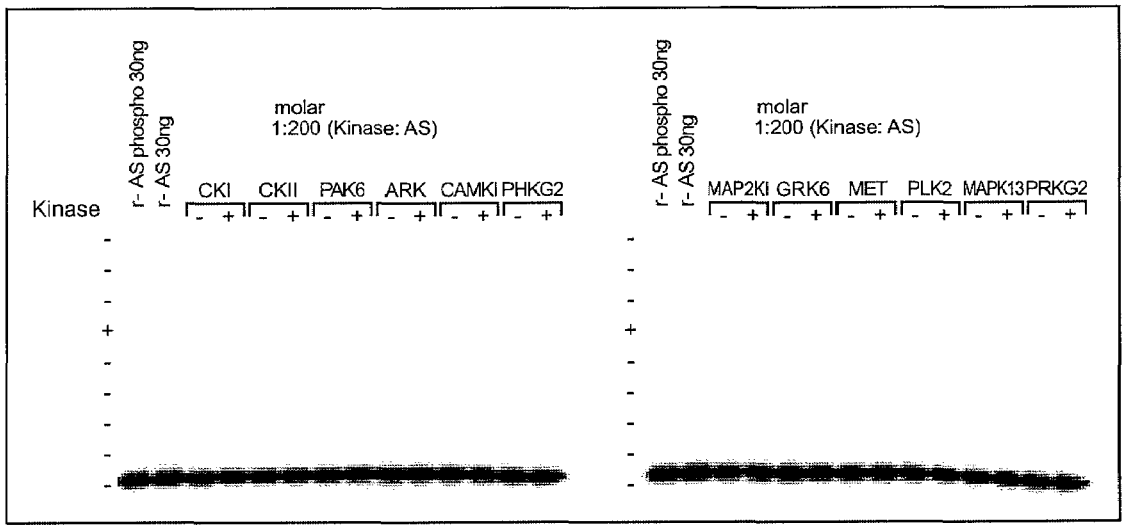
FIGS. 3A-C show the results of kinase activity in vitro for various kinases.
Figure 3B:
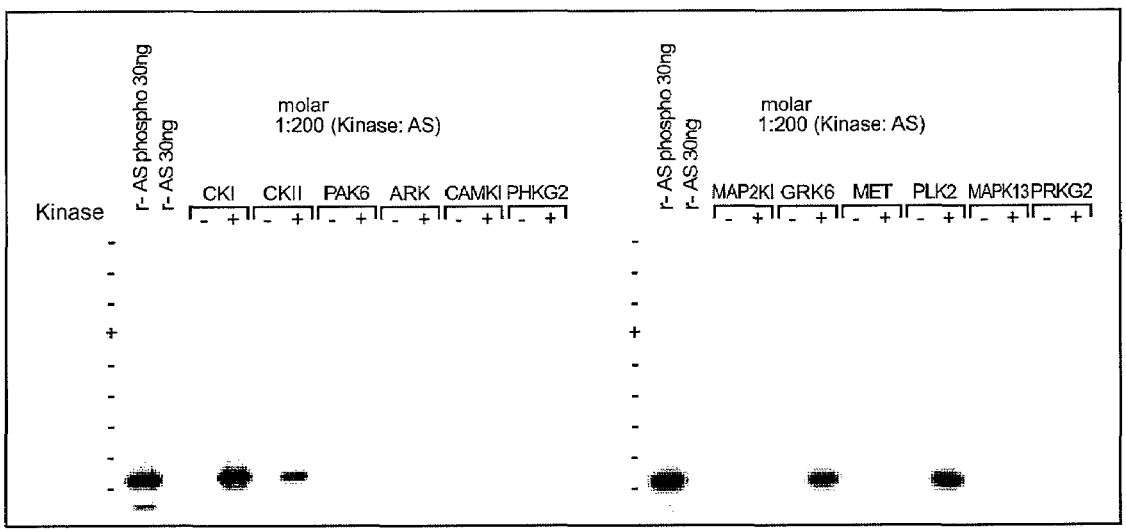
Figure 3C:
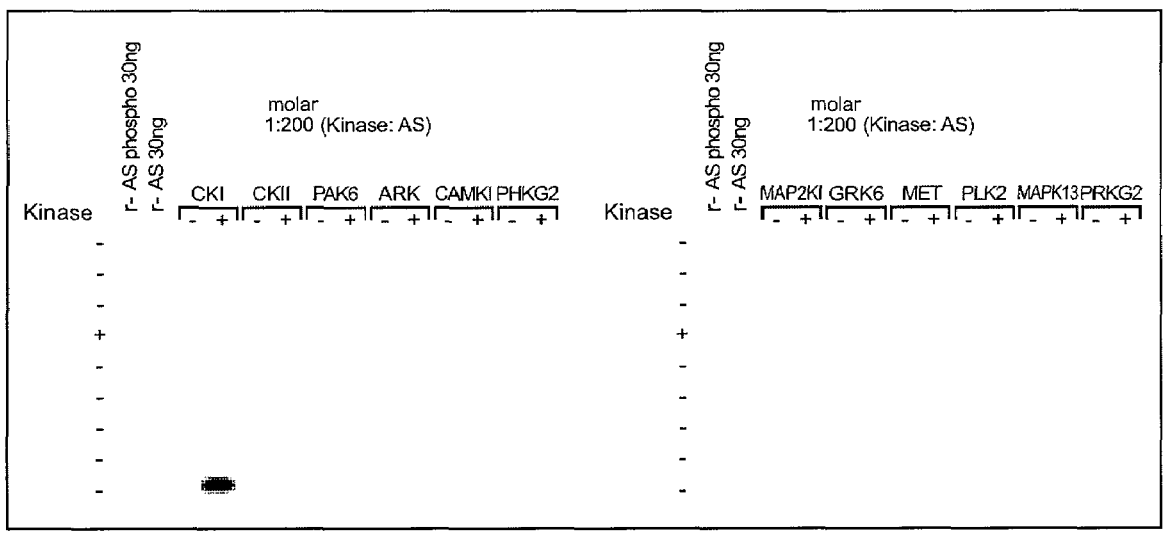

In the following examples, in vitro kinase assays were performed on a number of the potential targets identified in Examples 1 and 2. To correct for the activity bias, kinases were retested and newly procured kinases were put into an assay that normalized for molarity. This gave a better measurement of stoichiometric ratios between enzyme and substrate, thus reporting the phosphorylation event as a function of AS/kinase interaction. This was in contrast to the event in which unrelated substrate/kinase phosphorylation was measured. FIGS. 3A-C illustrate a more realistic view of AS phosphorylation with roughly equivalent levels of phospho ser-129 between CKI, GRK6 and PLK2 (one of 7 highly confirmed). CKII was reduced several-fold which is consistent with previous ELISA data using similar assay conditions. With the exception of CKI, none of the tested kinases were capable of phosphorylating AS at the ser-87 residue. This observation confirmed the specificity/preference of these kinases for the ser-129 site and/or the low preference/inaccessibility for the ser-87 site. However, CKI has been reported to phosphorylate at both sites.

Effect of Acidic Phospholipid on the Assay Results

Figure 4A:
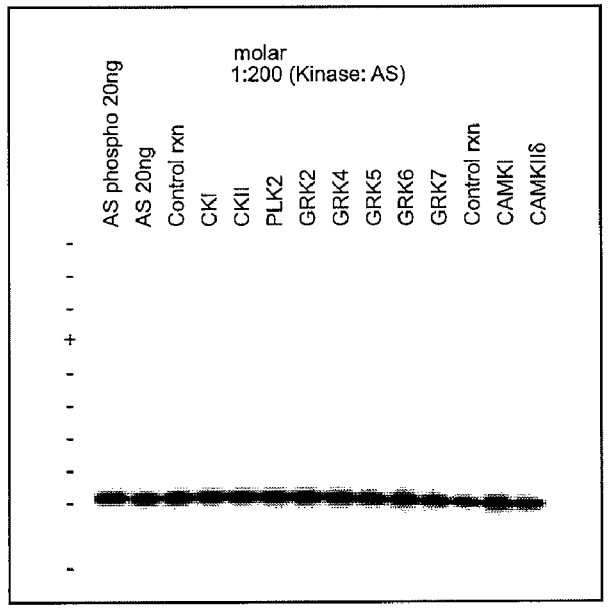
FIGS. 4A and B show the effect of phospholipid on the assay results in FIGS. 3A and 3B.
Figure 4B:
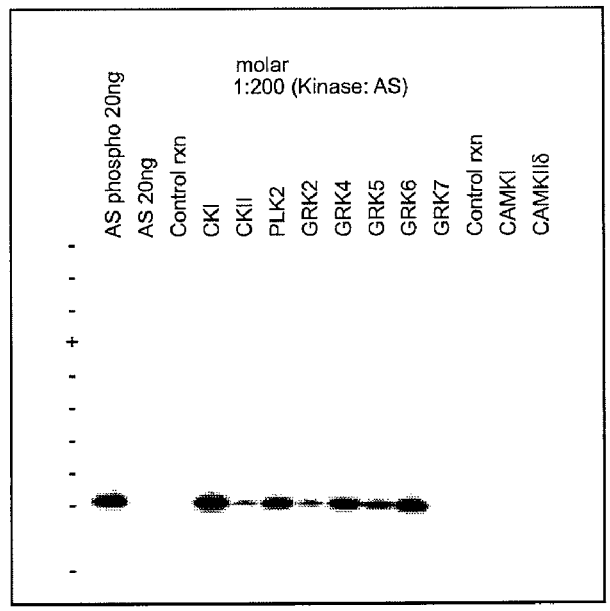
FIG. 4B shows Serine 129.

The significant levels of activity by GRK6 and PLK2 (polo-like kinase phylogenetically related to the GRK family) in the in vitro assay combined with the identification of PLK2, GRK2 and GRK1 as decreasers of phosphorylation in the RNAi screen, prompted a more comprehensive survey of other GRK members. FIGS. 4A and B indicate the results of GRK 2, 4, 5, 6, 7 and PLK2 compared in the in vitro assay. The results show a definite specificity for S129 phosphorylation in densitometry comparison. This preference could be represented as CKI>GRK6>PLK2>GRK4>GRK5>GRK2. GRK 7 was not able to phosphorylate at appreciable levels. All GRKs were unable to phosphorylate at ser-87 pointing to a specificity for the acidic sequence flanking amino acid 129. These reactions were quantitated and confirmed by ELISA measurements. These values more or less agreed with the immunoblot data with an apparent decrease in PLK2 level vs GRKs. It is likely that most of the AS substrate was depleted (phosphorylated) based on the assay design (300 ng AS, 210 nM for 17 hr) and the measured values represent a maximum OD/substrate in reaction.

The positive effect of acidic phospholipids on the phosphorylation of AS has been previously reported Pronin et. al. JBC 275(34): 26515-26522 (2000) and a pronounced effect on GRK 2 and 5 was observed. Because of this report and the many studies indicating that acidic phospholipids modulate AS conformation, a mixture of phosphatidylcholine (PC): phosphatidylserine (PS): phosphatidyl-inositol-phosphate-3 (PIP3) was generated and incorporated into the established in vitro assay. The lipid mixture was shown to increase signal for almost all of the kinases tested. The addition of a lipid environment is likely to imitate the membrane surface in a cell where AS and GRKs are likely to associate. Without being bound by the following theory, it is probably due to a favorable exposure of the C-term of AS upon lipid binding of the N-term helices of AS. Interestingly, the lipid effect of ser-87 phosphorylation (as see by the CKI reaction) led to a decrease in the level of phosphorylation. This may be the result of epitope masking by lipid interaction if ser-87 is buried upon helix interaction.

Example 4

Identification of Direct Phosphorylation of Alpha-Synuclein in Cell Lines

Figure 5:
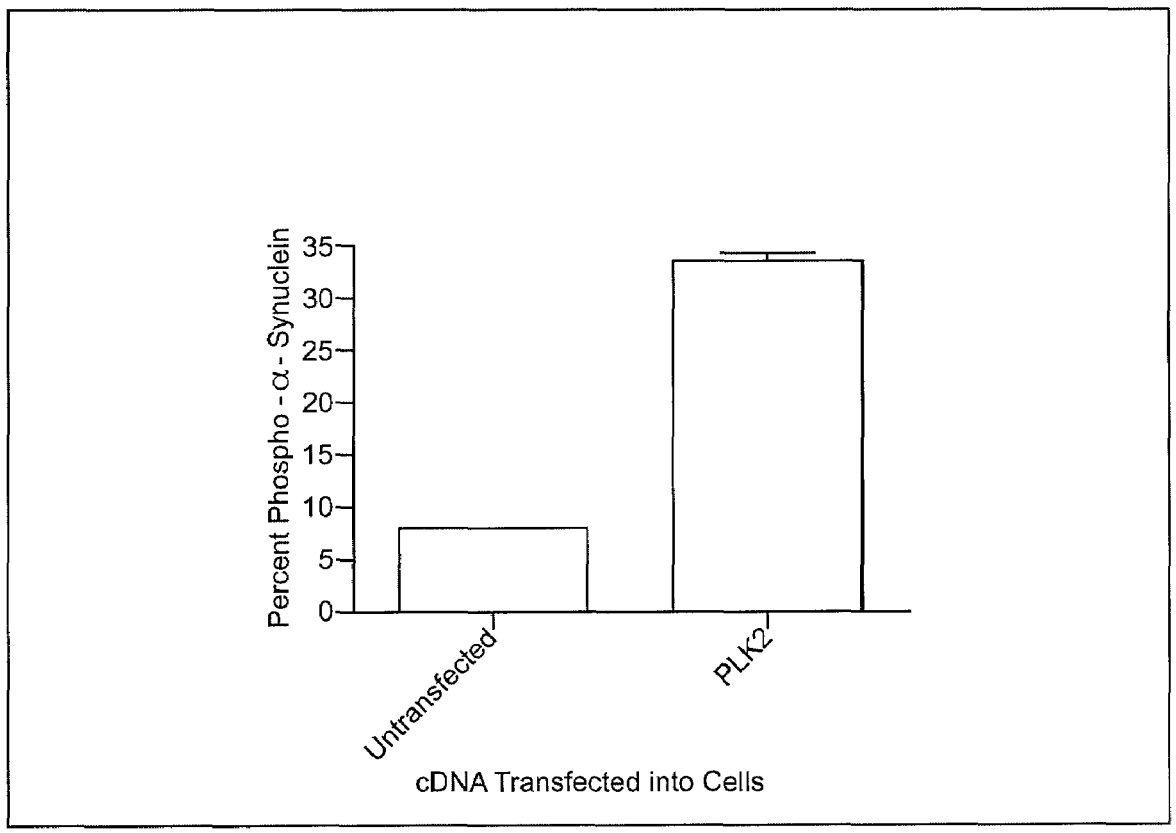
FIG. 5 shows the results of transfection of cDNA to PLK2 into 293-synuclein cells. Cells were analyzed by ELISA for total and phospho-synuclein levels.

Because kinases can be more promiscuous in vitro than they are in cells, an assay was performed in cell lines to confirm the direct interaction with alpha-synuclein. cDNAs for the kinases that phosphorylated alpha-synuclein in vitro from Example 3 were transfected into the PEAK-Syn cell line to see which was capable of phosphorylating alpha-synuclein ser-129 in cells. The results showed that GRK6 and even more profoundly PLK2 were able to mediate alpha-synuclein phosphorylation in cells (FIG. 5).

cDNA clones for PLK2, GPRK6, APEG1, CDC7 and PRKG1 were obtained from Origene. The cDNA was transcribed and transfected into PEAK-Syn cells using Lipofectamine 2000™ (Invitrogen). For each cDNA analyzed, 12 wells of a 96-well plate were transfected, along with 12 control wells of untransfected cells. Cells were harvested at 48 hrs post-transfection as per the ELISA screening protocol, and analyzed by ELISA for total and phospho-synuclein, and values were normalized for total protein. For those kinase targets not commercially available as recombinant proteins (namely APEG, PRKGI and CDC7LI), an in vitro cell-free reticulocyte system (Promega) was employed to express protein from human full-length cDNA clones (Origene). Proper sequence was determined and DNA prepared. PLK2 and GRK6 cDNA was also included in the study as positive controls.

The percentage of phospho-synuclein in untransfected cells was calculated to be 7.8%. The percentage of phospho-synuclein for the cells transfected with APEG1, CDC7 and PRKG1 cDNA was only marginally higher than untransfected cells at 8.9%. These kinases were considered to have produced a negative result in altering phospho-synuclein levels, and were considered negative controls for experimental purposes, as they were subjected to the same rigors of transfection that the other kinases were exposed to cDNA to PLK2 was transfected into 293-synuclein cells. Cells were harvested 48 hrs following transfection and analyzed by ELISA for total and phospho-synuclein levels. ELISA values were corrected for total protein levels. Overexpression of PLK2 resulted in a dramatic increase in phospho-synuclein levels, increasing phospho-synuclein expression by 4.3-fold above expression in untransfected cells.

Figure 6:
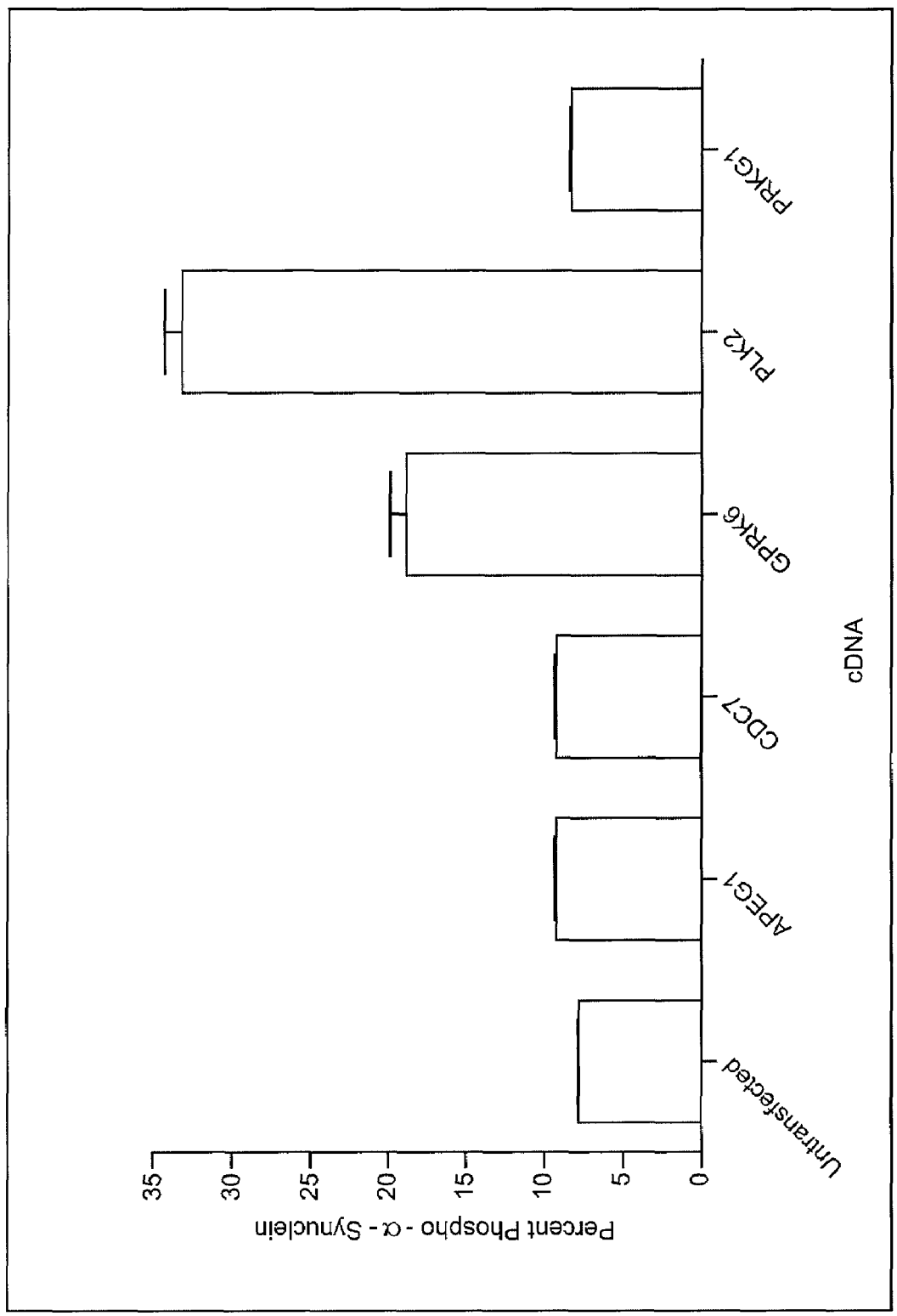
FIG. 6 shows the results of transfection of cDNA to GPRK6 and PLK2 into HEK-Synuclein cells.

It is likely that when a direct kinase that phosphorylates α-synuclein is introduced into the cell an increase in phospho-synuclein levels would be observed. This was the case for both GPRK6 and PLK2 (FIG. 6). The percent phospho-synuclein in cells transfected with GPRK6 cDNA increased dramatically, from 8.9% to 18.9%. This increase is significant to 9.25 standard deviations above the percent phospho-synuclein observed for the negative kinases. The increase in phospho-synuclein levels for the PLK2-transfected cells was even more dramatic, increasing the percent phospho-synuclein almost four-fold to 33.2%. This represents an extremely significant change, an increase of 22.75 standard deviations above the phospho-synuclein levels observed for the negative kinases. This dramatic increase was by far the largest change observed previously in using this assay. This data strongly indicates GPRK6, and especially PLK2 as very solid contenders as direct kinases responsible for phosphorylating α-synuclein. Thus, as shown in FIG. 6, when GPRK6 cDNA is transfected into HEK-synuclein cells, the expression of phospho-synuclein increases 2-fold. Introduction of PLK2 cDNA into cells results in an even more dramatic increase in phospho-synuclein expression, a change of almost four-fold above control values.

Example 5

Phosphorylation by PLK2 (SNK) GRK6, CKII and IKBKB

The data in Example 4 was further substantiated for PLK2 by showing that PLK2 siRNAs from a separate company (Dharmacon) also inhibited alpha-synuclein phosphorylation. This strengthened the data showing that PLK2 is a likely candidate as a cellular kinase that directly phosphorylates alpha-synuclein at Serine 129 (Tables 2 and 13).

Figure 7:
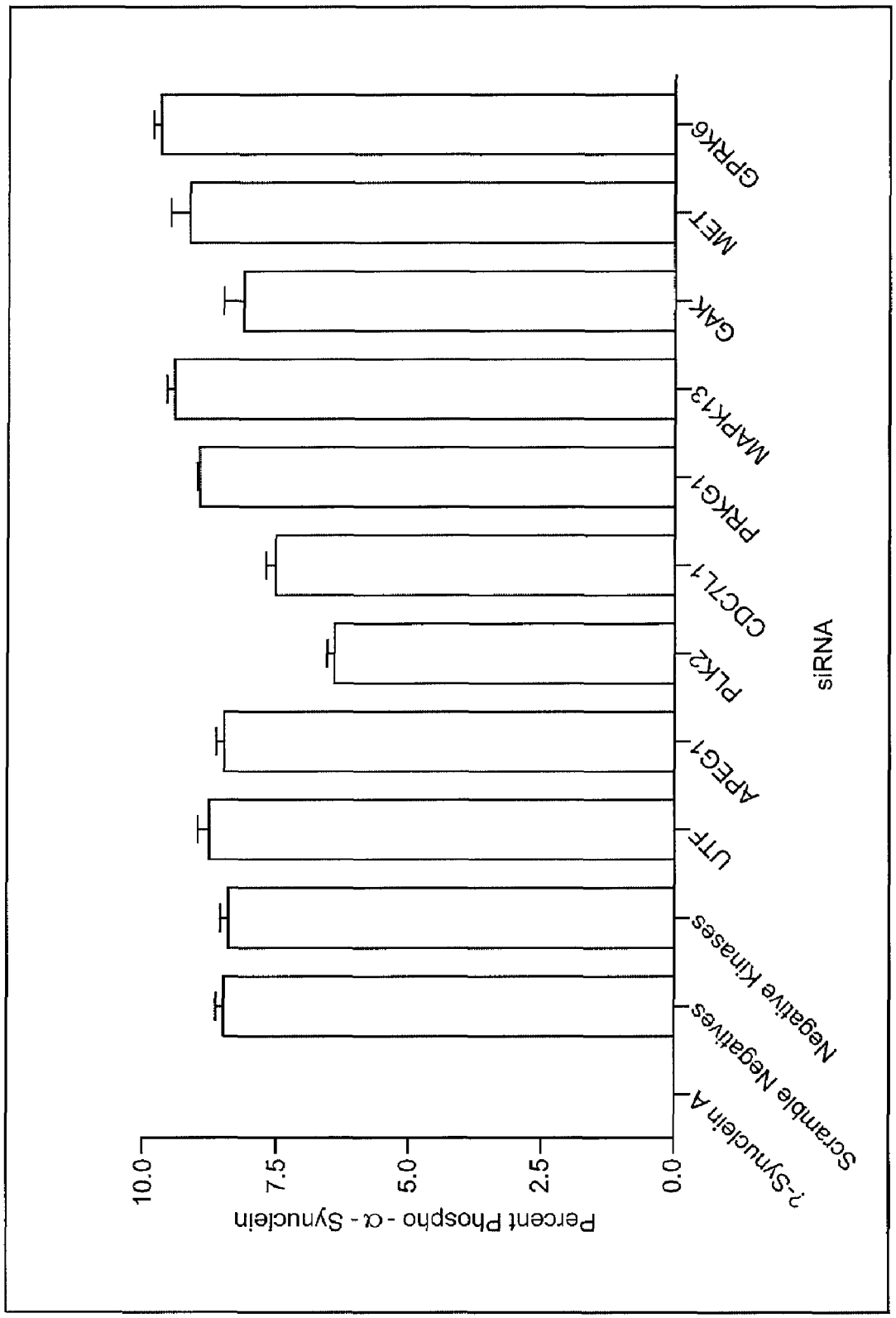
FIG. 7 shows that knockdown of the PLK2 siRNA from a second source causes a dramatic reduction in phospho-synuclein expression.

HEK 293 cells stably transfected with alpha-synuclein were transfected with 10 nM and 100 nM of SmartPool siRNAs. SmartPool siRNAs include 4 individual siRNAs to a specific target. Thus, the actual concentration of each of the four siRNAs transfected into cells was 2.5 nM and 25 nM respectively. The results in FIG. 7 show that PLK2 significantly decreased phospho-synuclein levels, a change of approximately 25%. At 10 nM, but not at 100 nM of siRNA, GPRK6 significantly increased the percentage of phospho-synuclein by one standard deviation above the mean of the control negative kinases (FIG. 7). This is the opposite effect to what was previously observed in the primary siRNA screen and may be due to the quality of the siRNA used in the first or second assays. These results were confirmed by immunohistochemistry.

The significant knockdown of phospho-synuclein levels by different siRNAs from a different source, independently confirms and solidifies the data, and substantiates the role of PLK2 as a direct kinase that phosphorylates α-synuclein. These Experiments were then performed on two other kinases identified in the screens to be of interest, casein kinase two (CKII) and IKBKB.

In vitro data provided herein suggests that although CKII does phosphorylate alpha-synuclein, it does not phosphorylate it as efficiently as PLK2. The individual CKII catalytic subunits were hits in the primary siRNA screen (see example 1 and Table 1B) and confirmed at the 10 mM siRNA screen. It was of interest to determine if the individual CKII subunits $\alpha^1$ and $\alpha'$, when cotransfected with PLK2 or each other, had additive effects on alpha-synuclein phosphorylation. Transfections were performed using the individual CKII subunits A ($\alpha^1$) and B ($\alpha'$), cotransfected with PLK2 or each other. Overexpression of these catalytic subunits increased phospho-synuclein levels by 1.75 and 1 standard deviations respectively (the effect was not additive). When each of the individual subunits was co-transfected with PLK2, the levels of phospho-synuclein increased over that of PLK2 alone (18.6% phospho-synuclein) by 1.25 standard deviations each to 22.8% phospho-synuclein. However when both subunits were co-transfected with PLK2 phospho-synuclein levels were not significantly increased above that for PLK2 alone (21.4% phospho-synuclein).

IKBKB siRNA knockdown resulted in a significant decrease in alpha-synuclein phosphorylation so this gene was tested for capacity to phosphorylate alpha synuclein. Transfections and ELISA analysis were performed as per standard procedure. Previous in vitro experiments demonstrated that IKBKB was not a direct synuclein kinase as it did not phosphorylate synuclein in a direct kinase assay (see Example 3), but may be an upstream regulator of synuclein phosphorylation. Thus, IKBKB was over-expressed in HEK-syn cells to identify the effect on phosphorylation of synuclein. Following introduction of IKBKB cDNA into cells, synuclein phosphorylation increased from 8.3% in the negative (empty vector) control to 21.5%, a 2.6-fold increase. This represented an increase in synuclein phosphorylation that was significant to almost 53 standard deviations. The PLK2 positive control increased synuclein phosphorylation to 65.8%, an almost 8-fold increase in phosphorylation (significant to 230 standard deviations). Although the effect on synuclein phosphorylation was much more modest for IKBKA, a related kinase, (1.2 fold) than for IKBKB, it was still significant to 1.4 standard deviations.

Example 6

Synphilin as an Alternative Therapeutic Target

Synphilin is a synuclein-associated protein that has been shown to bind alpha-synuclein. To determine if the presence of synphilin can enhance the phosphorylation of alpha-synuclein, it was over-expressed in HEK cells with and without alpha-synuclein and PLK2. Transfections were performed according to standard protocol, followed by alpha-synuclein ELISA and analysis. Cells were also harvested for Western blot analysis. Transfected cell lysates were analyzed for total synuclein using 1H7 antibody and phospho-serine 129 synuclein using 11A5 antibody. The total amount of DNA transfected into cells remained constant at 0.16 µg/well of a 96-well plate. The type of DNA introduced into cells varied, with empty vector being used to make up the full quota of DNA. Varying concentrations of alpha-synuclein, PLK2, and synphilin cDNA were introduced into naïve HEK cells. Cells transfected with all three showed a slight increase in total synuclein. For phospho-synuclein, the levels in untransfected cells were below the limit of quantitation. Introducing alpha-synuclein alone yielded 5.2% phospho-synuclein, which was marginally less than co-transfection of synuclein with synphilin (5.4% phospho-synuclein). Co-transfection of PLK2 and synuclein yielded levels similar those observed for transfecting PLK2 into HEK-syn stable cells, 60% phospho-synuclein. Strikingly, concurrent over-expression of all three cDNA's (PLK2, synuclein and synphilin) resulted in 83.3% phospho-synuclein in the HEK cells. Thus, synphilin increased synuclein phosphorylation in PLK2, alpha-synuclein over-expressed HEK cells.

Increased phosphorylation of alpha synuclein in the presence of synphilin can be explained by synphilin binding to the PLK2 polo-box thereby facilitating phosphorylation of synuclein by PLK2. Synuclein itself cannot bind the polo-box domain.

Example 7

PLK2 Activity Phosphorylation of Alpha Synuclein and Familial Mutants of Alpha Synuclein To analyze PLK2 phosphorylation of a number of known familial mutants of alpha synuclein, in vitro transfection studies were performed and the phosphorylation of the alpha synuclein and mutants analyzed. The familial mutants (FPD) were A30P, A53T, and E46K.

All in vitro reactions were performed using the following conditions, 10 mM MgC12, 100 µM ATP, 27 mM HEPES, 250 ng/ml PLK2, 1/50 dilution of Protease Inhibitor solution (1 tablet in 1 ml of reaction buffer), 40 mM Nitrophenylphosphate, 1 mg/ml of 95% Type II-S Phosphatidylcholine from soybean, and 10, 100, or 1000 nM alpha synuclein (AS). The reaction was incubated at 37° C. The activity was analyzed by autoradiography.

The transfections were conducted by plating 293 cells and treating with various amounts of PLK2 and alpha-synuclein DNA (using empty vector to keep total DNA constant) in Opti-MEM™ with Lipofectamine 2000™. Cells were harvested two days later in either sample buffer for Western blots, or 0.5 M guanidine with protease inhibitors for ELISAs using 11A5 antibody.

PLK2 was found to be more active against wild-type alpha synuclein than beta synuclein. Further, the mutant alpha-synuclein were phosphorylated more at a given concentration (especially at lower concentrations) than WT. The level of activity reflects a preference of the mutants and that the mutants have a lower Km than the WT. A trend of PLK2 activity was identified with PLK2 activity being highest with FPD mutants, followed by wild-type alpha synuclein, and minimally against beta synuclein. This order is consistent with a mechanism by which phosphorylation of alpha synuclein drives Lewy body formation and subsequent pathology.

Example 8

Figure 9A:
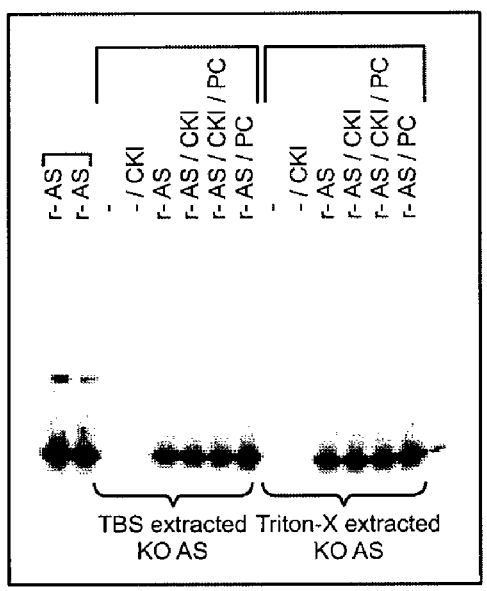
Figure 9B:
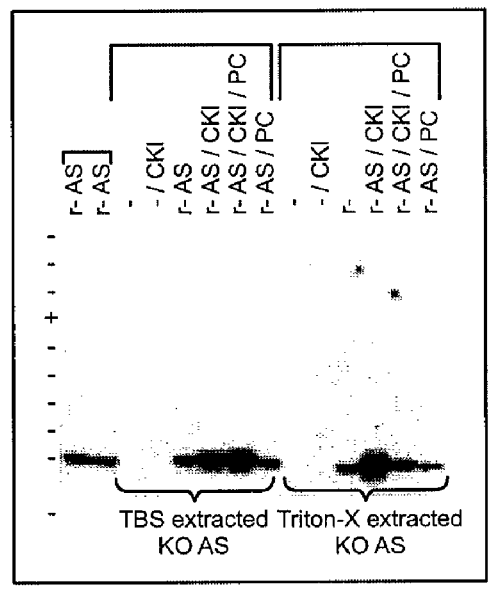

Confirmation of the Presence of Kinases in HEK-Synuclein and SY5Y-Synuclein Cells qRT-PCR was performed to determine if the kinases of interest were expressed in HEK-synuclein and SY5Y-synuclein cells. In Table 16 all samples were normalized to GAPDH expression. In addition, two of the negative kinases were analyzed in each experiment as a reference. Of the 24 potential direct kinase candidates tested, 20 were detected in the HEK293-synuclein cells, including PLK2. Thus, the remaining completely confirmed kinases were detected in the cells (FIG. 9). Four of the potential direct kinases tested, GPRK1, GPRK7, ERK8 and RIPK3, were not detected. GPRK6 was barely detectable.

The qRT-PCR was performed as follows: the mRNA levels were normalized to GAPDH mRNA expression levels. Total RNA was purified from a cell pellet using the QIAGEN RNeasy Kit and protocol. Primer-probe sets for 24 of the potential direct kinases and the four indirect completely confirmed kinases were ordered from Applied Biosystems (TaqMan Gene Expression Assays), along with reverse transcriptase, RNase inhibitors and standard PCR reagents. A one-step RT-PCR/qRT-PCR reaction as performed an ABI7500 Real-Time PCR machine for each primer-probe set using 20 ng or 200 ng total RNA using the following cycling conditions: 48° C./30 mins (RT-PCR step), 95° C./10 mins (denature), then 40 cycles of 95° C./15 secs, 60° C./1 min. For each primer-probe set, an RT-negative reaction and PCR-negative reaction was performed. The RT-negative controls for background amplification of DNA (not RNA) that is contaminating the purified RNA. The PCR-negative control was to ensure all of the PCR reagents were free of contaminating RNA and DNA, and should have had no signal.

All three of the completely confirmed potential direct kinases, along with the four indirect completely confirmed kinases were easily detected in SY5Y-synuclein cells, indicating this cell line may be a viable option for a neuronally-derived cell line for further experimental analysis of kinases.

TABLE 16 qRT-PCR demonstration of the presence of kinases in HEK-synuclein and SY5Y-synuclein cells

| Sample Name | Relative Expression (to GAPDH) |
|---|---|
| SYN APEG1 | 2.23 |
| SYN SNK/PLK2 | 3.57 |
| SYN CDC7L1 | 1758.34 |
| SYN PRKG1 | 7.36 |
| SYN MAPK13 | 8.97 |
| SYN GAK | 2.17 |
| SYN MET | 891.44 |
| SY5Y-SYN APEG1 | 1698.45 |
| SY5Y-SYN SNK/PLK2 | 208.66 |
| SY5Y-SYN CDC7L1 | 24.42 |
| SY5Y-SYN PRKG1 | 42.22 |
| SY5Y-SYN MAPK13 | 45.73 |
| SY5Y-SYN GAK | 17.63 |
| SY5Y-SYN MET | 86.22 |

Example 9

Identification of Increased Phosphorylation of Alpha-Synuclein in 293 cells and Neuronally-Derived Cell Lines PLK and GRK were overepressed in 293 cells stably transfected with alpha synuclein. ELISA and Western blot were performed to identify increase in phospho-synuclein with PLK and GRK kinases and an increase in phosphorylation was demonstrated. A second method was used to confirm the increase using the same biotinylated antibodies used in the ELISA for immunostaining (11A5) in 293 cells. This method also demonstrated an increase in phospho-synuclein in cells transfected with PLK2 and to a lesser extent GRK. The increase was detected in a small population of cells that brightly stain for 11A5, not a general increase in all cells. The amount of total synuclein (measured using the 5C12 antibody) did not appear to change. This was a significant increase in phosphorylation in the 293 cells. Thus, it was of interest to see if the results could be repeated in neuroblastoma cells.

To identify that the dramatic upregulation of phospho-synuclein observed with PLK2 and GPRK6 occurs in neuronally-derived cells, the same experiment was performed in human neuroblastoma cells (SY5Y cells). Immunostaining results showed that PLK2 caused an increase in the phospho-synuclein in a small population of cells, in a very similar pattern to the 293 cell experiments. Quantitation was performed by immunohistochemistry using the ArrayScan™ in two ways. First all cells were counted and did not show any difference. Then just the bright cells were counted and this analysis showed about a 5-10 fold increase in the number of 11A5 positive cells that were PLK transfected, with a slight increase with GRK6 as well.

The cDNA transfection experiment is repeated in HCC cells and immunohistochemistry is performed with a variety of alpha-synuclein antibodies on the cells that have been transfected with PLK2 and GPRK6. In this way, inclusion formation and/or alpha-synuclein aggregation is observed in these cells. Antibodies used to look for inclusions/aggregation include LB509, SYN-1, 11A5 and ELADW-110.

Next, cDNA for PLK2 and GPRK6 siRNA is transfected in primary neuronal cultures in preparation for introducing targets into a mouse model. The method is performed as in Example 4. qRT-PCR is performed (as in Example 2) using SY5Y-synuclein RNA. SY5Y-synuclein cells are derived from neuroblastoma cells and have been stably transfected with a WT-synuclein vector.

Example 10

Identification of Involvement of PLK2 in Cell Cycle Regulation

Because PLK2 is a G1 phase cell cycle regulation protein, it is of interest to identify whether PLK2 phosphorylation of alpha-synuclein results in a change in cell cycle regulation. A decrease in the percentage of phospho-synuclein in cells as they grow more confluently was previously observed (as growth slows down). This fits very well with one or more direct kinases that phosphorylate alpha-synuclein being involved in cell cycle regulation. As such, one or more antibodies to PLK2 are used to analyze normalized protein levels by Western blot to determine if decreased PLK2 levels correlate with this observed decrease in phospho-synuclein levels and cell confluency.

Example 11

Distribution of Lentivirus-Expressed Alpha-Synuclein in Human Cortical Culture (HCC)—A Cellular Model for Lewy Body Disease Of interest was the identification of a cellular model for Lewy body disease and/or for PD pathology. Thus, lentivirus-mediated expression of alpha-synuclein in human cortical cultures was used to establish a model of alpha-synuclein deposition in vivo. As such, experiments were performed on donors, and HCC cells overexpressing wild-type and variant alpha-synuclein to fractionate the cells and localize wild-type alpha-synuclein and variant alpha-synuclein within the cells. The results below show that the HCC cells showed aggregation of alpha synuclein in a manner matching LB disease. Further, when PLK2 was expressed, the phosphorylation of alpha-synuclein as well as the aggregation increased.

Further experiments were performed to identify whether extending culture might increase the accumulation of overexpressed synuclein, and would stress the cells, which also might favor synuclein deposition or toxicity. Accordingly, HCC were transduced with viral vectors expressing WT, A53T, S129A or both A53T/S129A alpha-synuclein mutants. Following transfection cells were grown in vitro for 9, 16 or 23 days before collecting and fractionating. ELISA results were normalized to protein concentration and showed an accumulation of synuclein in the soluble fraction with increasing time. Somewhat greater accumulation was observed with the S129A mutant.

When further experiments were performed with wt, 119-truncated, and E46K AS, the results were as follows. The higher the expression of wild-type the larger the portion of alpha synculein recovered in the soluble fraction. E46K synuclein showed a 50-100% increase in the amount of phosphorylated alpha-synuclein. However, the E46K mutation did not markedly affect relative amounts of synuclein recovered in the membrane-bound or insoluble fractions. Expression of 119 alpha synuclein led to a slight increase in the relative amount accumulating in the insoluble fraction (about 3 fold higher relative to WT). The increase is expected in view of the published results suggesting that truncated synuclein forms fibrils much more readily in vitro than does full-length (Murray et al. 2003 Biochemistry 42:8530). The 119 truncation resulted in an increased association with membranes consistent with the N-terminal domain being responsible for association with lipid bilayers. The increased association with membranes may mitigate the increased tendency of the soluble protein to aggregate. The response of the insoluble fraction to increases in levels of soluble synuclein on overexpression and to truncation, a change favoring aggregation, suggest that it provides a way to identify factors affecting aggregation in the intraneuronal milieu.

Additional experiments are performed to determine if the CHAPS-resistant, UTC-extractable alpha-synuclein resembles PD and/or DLB pathology (Lewy inclusions). For example, the same experiments are done with beta-synuclein since beta synuclein is not associated with Lewy inclusions and does not aggregate in vitro.

The increased alpha-synuclein in the soluble compartment might be shifting the alpha-synuclein to a potentially more vulnerable compartment, leading to changes which could result in increased deposition. Since the kinases proposed to phosphorylate alpha-synuclein at Ser129 are soluble, it seems likely that the soluble alpha-synuclein is more accessible to phosphorylation as well.

Additional experiments are performed to identify inhibitors of the phosphorylation and/or aggregation in this cellular model by expressing the inhibitors in the cells and identifying a reduction in the phosphorylation and/or aggregation.

Example 12

Analysis of Endogenous Kinase Activity in Alpha-Synuclein KO Mouse

Figure 8A:
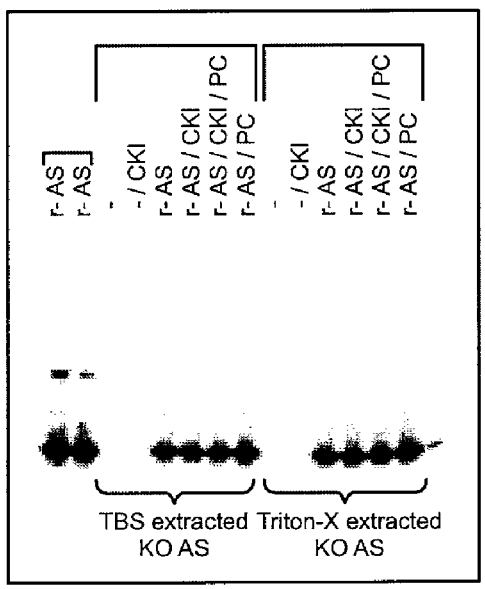
FIGS. 8A and 8B and 9A and 9B show the in vitro phosphorylation of alpha-synuclein by putative kinase targets in alpha-synuclein KO mouse brain.
Figure 8B:
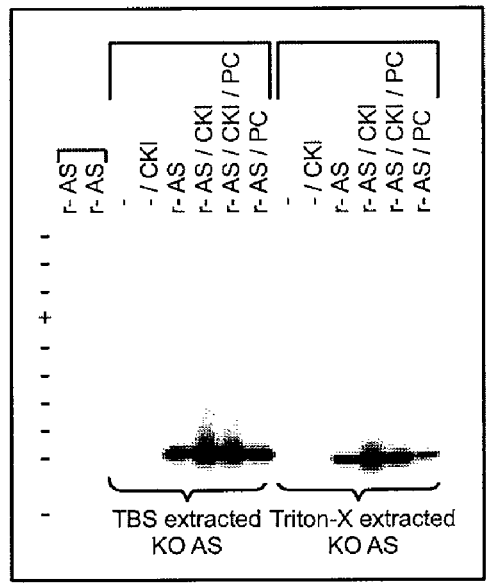

The utilization of an alpha-synuclein knockout (alpha-synuclein KO) mouse brain for the identification of a putative alpha-synuclein kinase has the advantage over the siRNA screen in the following ways: 1) the use of brain material which will provide relevant and possibly higher levels of brain-specific kinase activity which the HEK cell line may not provide, 2) cofactors present in brain (lipid, protein, etc.) which may not be present in cells and 3) absence of any endogenous alpha-synuclein which could be detected as a phosphorylated AS. The inclusion of 25-50 µg of extracts (soluble and detergent soluble) with recombinant alpha-synuclein (rAS) was assessed with 250 µM ATP to determine if appreciable kinase activity was present in crude material. FIG. 8A shows total alpha-synuclein in each reaction indicating equivalent loadings of rAS. In FIG. 8B, the levels of phospho-ser-129 alpha-synuclein were investigated. The rAS in both TBS (sucrose soluble) and TX extracts was phosphorylated, with roughly twice the level of signal from the TBS material than the TX (although reactions were not normalized for protein). Phosphorylation levels were increased by addition of CKI but were not significantly affected by the addition of phospholipids from soybean. An identical blot was probed for ser-87 phosphorylation in FIG. 9B. This pAb presents cross-reactivity with rAS at 100 ng thus levels above background indicate true phosphorylation at theS87 site. In both TBS and TX reactions there is no significant phosphorylation at this site whereas the CKI spike achieved phosphorylation at appreciable levels. These experiments suggest that measurable and real kinase activit(ies) are present in the soluble and membrane fractions of KO mouse brain and are specific to the S129 site compared to S87. The potential exists for phosphorylation at other serine or threonine sites in alpha-synuclein but antibodies are not yet available to detect such modifications. Thus, measurable levels of ser-129 specific kinase activity/activities are present in alpha-synuclein KO mouse brain extracts and could serve as starting material for purification of a kinase from the brain.

In FIGS. 8A, 8B, 9A and 9B, cortices of alpha-synuclein KO mouse brain were Dounce homogenized to obtain 200 mM sucrose soluble and 0.1% Triton X-100 soluble extracts with protease and phosphatase inhibitors present. 20 µl of sample (100 µl total volume of reaction) was incubated with 2.4 µg of wt-rAS in the presence or absence of 1000 units of casein kinase I(CKI) as a positive control, and/or 200 µg of phosphatidycholine (PC; soybean lecithin) to increase kinase activiti(es). Reactions were loaded on SDS-PAGE (130 ng total AS) and immunoblotted with Syn-1 (total Syn; 0.1 ug/ml), 11A5 (phospho ser-129; 1 µg/ml) or ELADW110 (phospho ser-87; 2 µg/mL).

The above data shows that PLK2 other direct and/or indirect kinases (such as GRK6), and modulators such as synphilin are novel targets for therapeutic intervention in DLB and PD. PLK2 is a preferred target because it can directly phosphorylate alpha-synuclein specifically at ser-129.

The above examples are illustrative only and do not define the invention; other variants will be readily apparent to those of ordinary skill in the art. The scope of the invention is encompassed by the claims of any patent(s) issuing herefrom. The scope of the invention should, therefore, be determined not with reference to the above description, but instead should be determined with reference to the issued claims along with their full scope of equivalents. All publications, references (including accession numbers), and patent documents cited in this application are incorporated by reference in their entirety for all purposes to the same extent as if each individual publication or patent document were so individually denoted.

What is claimed is:

1. A method for producing alpha-synuclein phosphorylated at serine 129 comprising:

providing a plasmid encoding alpha-synuclein and a plasmid encoding PLK2 in a bacterial cell;

culturing the cell whereby the plasmids are co-expressed to produce alpha-synuclein and PLK2 in the cell, whereby the PLK2 phosphorylates the alpha-synuclein in the cell; and isolating alpha-synuclein from the cell, wherein the isolated alpha-synuclein comprises alpha-synuclein phosphorylated at serine 129.

2. The method of claim 1 wherein more than 95% of the isolated alpha-synuclein is phosphorylated at serine 129.

3. The method of claim 1 wherein said isolating comprises (i) preparing a lysate of said bacteria and (ii) boiling said lysate.

4. A method for producing human synuclein phosphorylated at serine 129 comprising co-expressing recombinant human alpha-synuclein and recombinant human PLK2 in a bacterial cell under conditions in which at least a portion of the expressed alpha-synuclein is phosphorylated at serine-129.

5. The method of claim 4 further comprising isolating alpha-synuclein from the cell, wherein the isolated alpha-

SEQUENCE LISTING

```
<160> NUMBER OF SEQ ID NOS: 1

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
``` synuclein comprises alpha-synuclein phosphorylated at serine-129.

6. The method of claim 5 wherein more than 95% of the isolated alpha-synuclein is phosphorylated at serine-129.

7. The method of claim 5 wherein said isolating comprises (i) preparing a lysate of said bacteria and (ii) boiling said lysate.

* * * * *

UNITED STATES PATENT AND TRADEMARK OFFICE
CERTIFICATE OF CORRECTION

PATENT NO. : 7,553,639 B2 Page 1 of 1
APPLICATION NO. : 11/669093
DATED : January 30, 2007
INVENTOR(S) : David Chereau It is certified that error appears in the above-identified patent and that said Letters Patent is hereby corrected as shown below:

Title page, item [75] delete inventors "Tamie J. Chilcote, Kelly Banducci, Normand L. Frignon, Guriqbal S. Basi, John P. Anderson, Jason Goldstein, and Irene Griswold-Prenner"

Signed and Sealed this

Twenty-seventh Day of July, 2010

David J. Kappos
*Director of the United States Patent and Trademark Office*